United States Patent
Gelinas et al.

(10) Patent No.: US 9,096,668 B2
(45) Date of Patent: *Aug. 4, 2015

(54) METHODS FOR MAKING ANTIBODY MOLECULES HAVING SPECIFICITY FOR HUMAN IL-6

(71) Applicant: UCB Pharma S.A., Slough, Berkshire (GB)

(72) Inventors: Richard Evan Gelinas, Seattle, WA (US); Mitra Choudhury Singhal, Seattle, WA (US); Yi Zhang, Palo Alto, CA (US); Andrew George Popplewell, Slough (GB); Ralph Adams, Slough (GB)

(73) Assignee: UCB PHARMA S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/928,458

(22) Filed: Jun. 27, 2013

(65) Prior Publication Data

US 2014/0024077 A1    Jan. 23, 2014

Related U.S. Application Data

(60) Continuation of application No. 13/288,260, filed on Nov. 3, 2011, now Pat. No. 8,486,662, which is a division of application No. 11/608,408, filed on Dec. 8, 2006, now Pat. No. 8,075,889.

(60) Provisional application No. 60/748,926, filed on Dec. 9, 2005.

(51) Int. Cl.

| | | |
|---|---|---|
| *C12N 15/09* | (2006.01) | |
| *C12P 21/08* | (2006.01) | |
| *C07K 16/24* | (2006.01) | |
| *A61K 39/00* | (2006.01) | |

(52) U.S. Cl.
CPC ......... *C07K 16/248* (2013.01); *A61K 2039/505* (2013.01); *C07K 2316/96* (2013.01); *C07K 2317/24* (2013.01); *C07K 2317/34* (2013.01); *C07K 2317/54* (2013.01); *C07K 2317/55* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. | |
| 5,219,996 A | 6/1993 | Bodmer et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,545,806 A | 8/1996 | Lonberg et al. | |
| 5,569,825 A | 10/1996 | Lonberg et al. | |
| 5,571,698 A | 11/1996 | Ladner et al. | |
| 5,580,717 A | 12/1996 | Dower et al. | |
| 5,585,089 A | 12/1996 | Queen et al. | |
| 5,618,700 A | 4/1997 | Novick et al. | |
| 5,625,126 A | 4/1997 | Lonberg et al. | |
| 5,633,425 A | 5/1997 | Lonberg et al. | |
| 5,658,727 A | 8/1997 | Barbas et al. | |
| 5,661,016 A | 8/1997 | Lonberg et al. | |
| 5,667,425 A | 9/1997 | Pineau et al. | |
| 5,698,426 A | 12/1997 | Huse | |
| 5,733,743 A | 3/1998 | Johnson et al. | |
| 5,750,753 A | 5/1998 | Kimae et al. | |
| 5,770,429 A | 6/1998 | Lonberg et al. | |
| 5,780,225 A | 7/1998 | Wigler et al. | |
| 5,821,047 A | 10/1998 | Garrard et al. | |
| 5,856,135 A | 1/1999 | Tsuchiya et al. | |
| 5,969,108 A | 10/1999 | McCafferty et al. | |
| 7,291,721 B2 | 11/2007 | Komar et al. | |
| 8,486,662 B2 * | 7/2013 | Gelinas et al. | 435/69.6 |

FOREIGN PATENT DOCUMENTS

| | | |
|---|---|---|
| EP | 0392745 B1 | 11/1994 |
| EP | 0438474 B1 | 5/1996 |
| EP | 0463151 B1 | 6/1996 |
| EP | 0546073 B1 | 9/1997 |
| EP | 0983767 B1 | 3/2000 |
| EP | 0948544 B1 | 5/2003 |
| EP | 1090037 B1 | 11/2004 |
| EP | 1536012 A4 | 6/2005 |
| WO | WO86/15333 A1 | 3/1986 |
| WO | WO87/04462 A1 | 7/1987 |
| WO | WO89/00195 A1 | 1/1989 |
| WO | WO89/01476 A1 | 2/1989 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A2 | 12/1992 |
| WO | WO93/06231 A1 | 4/1993 |
| WO | WO93/11236 A1 | 6/1993 |

(Continued)

OTHER PUBLICATIONS

De Pascalis et al. Grafting of "abbreviated" complementarity-determining regions containing specificity-determining residues essential for ligand contact to engineer a less immunogenic humanized monoclonal antibody. J. Immunol. 2002, 169:3076-3084.*

(Continued)

*Primary Examiner* — Dong Jiang

(74) *Attorney, Agent, or Firm* — Saul Ewing, LLP

(57) ABSTRACT

The invention relates to antibody molecules having specificity for antigenic determinants of IL-6, therapeutic uses of the antibody molecules and methods for producing said antibody molecules.

3 Claims, 10 Drawing Sheets

(56) References Cited

FOREIGN PATENT DOCUMENTS

| | | |
|---|---|---|
| WO | WO95/15982 A2 | 6/1995 |
| WO | WO95/20401 A1 | 8/1995 |
| WO | WO98/20734 A2 | 5/1998 |
| WO | WO98/25971 A1 | 6/1998 |
| WO | WO03/031581 A2 | 4/2003 |
| WO | WO2004/039826 A1 | 5/2004 |
| WO | WO2004/051268 A1 | 6/2004 |
| WO | WO2004/072116 A2 | 8/2004 |
| WO | WO2004/106377 A1 | 12/2004 |
| WO | WO2005/003169 A3 | 1/2005 |
| WO | WO2005/003170 A3 | 1/2005 |
| WO | WO2005/003171 A3 | 1/2005 |
| WO | WO2005/113605 A1 | 12/2005 |
| WO | WO2005/117984 A3 | 12/2005 |
| WO | WO2006/119115 | 11/2006 |

OTHER PUBLICATIONS

Adair, J.R., et al., "Therapeutic antibodies," Drug Design Reviews—Online 2005, vol. 2, No. 3, pp. 209-217.
Akira, S. et al., Biology of multifunctional cytokines: IL 6 and related molecules (IL 1 and TNF) FASEB J., vol. 4, pp. 2860-2867 (1990).
Ames, R.S. et al., "Conversion of murine Fabs isolated from a combinatorial phage display library to full length immunoglobulins," J. Immunol. Methods, vol. 184, pp. 177-186 (1995).
Angal, S. et al., "A single amino acid substitution abolishes the heterogeneity of chimeric mouse/human (IgG4) antibody," Molecular Immunology, vol. 30, No. 1, pp. 105-108 (1993).
Atreya, R. et al., "Blockade of interleukin 6 trans signaling suppresses T-cell resistance against apoptosis in chronic intestinal inflammation: evidence in Crohn disease and experimental cotitis in vivo," Nature Amer., vol. 6, No. 5, pp. 583-588 (2000).
Babcook, J. et al., "A novel strategy for generating monoclonal antibodies from single, isolated lymphocytes producing antibodies of defined specificities," Proc. Natl. Acad. Sci. USA, vol. 93, pp. 7843-7848 (1996).
Baxter, N.J. et al., Temperature dependence of H chemical shifts in proteins, J. Biomol. NMR, vol. 9, pp. 359-369 (1997).
Bock, G.H., et al., "Characterization of a new IL-6-dependent human B-lymphoma cell line in long term culture," Cytokine, vol. 5, No. 5, pp. 480-489 (1993).
Boder, E.T. et al., "Directed evolution of antibody fragments with monovalent femtomolar antigen-binding affinity", vol. 97, No. 20, pp. 10701-10705, 2000.
Boulanger, M.J. et al., "Hexameric structure and assembly of the interleukin-6/IL-6 α-receptor/gpl30 complex," Science, vol. 300, pp. 2101-2104 (2003).
Brakenhoff, J.P.J. et al., "Structure-function analysis of human IL-6; epitope mapping of neutralizing monoclonal antibodies with amino- and carboxyl-terminal deletion mutants," J. of Immunology, vol. 145, No. 2, pp. 561-568 (1990).
Bravo, J. et al., "New EMBO members' review: Receptor recognition by gp130 cytokines," EMBO J., vol. 19, No. 11, pp. 2399-2411 (2000).
Brinkman, U. et al., "Phage display of disulfide-stabilized Fv fragments," J. Immunol. Methods, vol. 182, pp. 41-50 (1995).
Burton, D.R. et al., "Human antibodies from combinatorial libraries," Advances in Immunology, vol. 57, pp. 191-280 (1994).
Chapman, A., "PEGylated antibodies and antibody fragments for improved therapy: a review," Advanced Drug Delivery Reviews, vol. 54, pp. 531-545 (2002).
Chomarat, P. et al., "IL-6 switches the differentiation of monocytes from denditic cells to macrophages," Nature Immunol., vol. 6, pp. 510-514 (2000).
Chothia, C. et al., "Canonical structures for the hypervariable regions of immunoglobulins," J. Mol. Biol., vol. 196, 901-917 (1987).
Cole, S.P.C. et al., "The EBV-hybridoma technique and its application to human lung cancer," Monoclonal Antibodies & Cancer Therapy, Proceedings of the Roche-UCLA Symposium, Alan R. Liss, Inc., pp. 77-96 (1985).
Crameri, A. et al., "DNA shuffling of a family of genes from diverse species accelerates directed evolution," Nature, vol. 391, pp. 288-291 (1998).
Database Uniprot (Online), "IL-6 Human", Database accession No. P05231 (1987).
Delaglio, F. et al., "NMRPipe: a multidimensional spectral processing system based on UNIX pipes," J. Biomol. NMR, vol. 6, pp. 277-293 (1995).
De Pascalis, et al., "Grafting of 'abbreviated' complementarity-determining regions containing specificity-determining residues essential for ligand contact to engineer a less immunogenic humanized monoclonal antibody", J. Imunol., vol. 169, pp. 3076-3084, (2002).
Dubowchik, G.M. et al., "Receptor-mediated and enzyme-dependent targeting of cytotoxic anticancer drugs," Pharmacology & Therapeutics, vol. 83, pp. 67-123 (1999).
Farmer, B.T. et al., "Localizing the $NADP^+$ binding site on the MurB enzyme by NMR," Nat. Struct. Mol. Biol., vol. 3, No. 12, pp. 995-997 (1998).
Finck, B.K. et al., "Interleukin 6 promotes murine lupus in NZB/NZW $F_1$ mice," J. Clin. Invest., vol. 94, pp. 585-591 (1994).
Gejima, R. et al., "Human single-chain Fv (scFv) antibody specific to human IL-6 with the inhibitor activity on IL-6 signaling," vol. 11, pp. 121-129 (2002).
Grossman, R.M. et al., "Interleukin 6 is expressed in high levels in psoriatic skin and stimulates proliferation of cultured human keratinocytes," Prot. Natl. Acad. Sci., vol. 86, pp. 6367-5371 (1989).
Grzesiek, S. et al., "Improved 3D triple-resonance NMR techniques applied to a 31 kDa protein," J. Biomol. NMR, vol. 96, pp. 432-440 (1992).
Grzesiek, S., et al., "Amino acid type determination in the sequential assignment procedure of uniformly $^{13}C/^{15}N$-enriched proteins," J. Biomolecular NMR, vol. 3, pp. 185-204 (1993).
Hansen, M.B. et al., "Influence of interleukin-6 (IL-6) autoantibodies on IL-6 binding to cellular receptors," Eur. J. Immunol., vol. 25, No. 2, pp. 348-354 (1995).
Harris, R.J., "Processing of C-terminal lysine and arginine residues of proteins isolated from mammalian cell culture," J. of Chromatography A, vol. 705, pp. 129-134 (1995).
Hellstrom, K.E. et al., "Antibodies for drug delivery," Controlled Drub Delivery, Robinson, et al., eds, Marcel Dekker, Inc., Ed. 2, Chapter 15, pp. 623-653 (1987).
Hieter, P.A. et al., "Evolution of Human Immunoglobulin K J Region Genes," J. Biol. Chem., vol. 257, No. 3, pp. 1516-1522 (1982).
Hirano, T. et al., "Complementary DNA for a novel human interleukin (BSF-2) that induces B lymphocytes to produce immunoglobulin," Nature, vol. 324, pp. 73-76 (1986).
Holliger, P. et al., "Engineered antibody fragments and the rise of single domains," Nature Biotech., vol. 23, No. 9, 1126-1136 (2005).
Horii, Y. et al., "Involvement of IL-6 in mesangial proliferative glomerulonephritis," J. Immunol., vol. 142, pp. 3949-3955 (1989).
Kalai, M. et al., "Analysis of the mechanism of action of anti-human interleukin-6 and anti-human interleukin-6 receptor-neutralising monoclonal antibodies," Eur. J. Biochem., vol. 249, pp. 690-700 (1997).
Kashmiri, S.V.S. et al., "SDR grafting—a new approach to antibody humanization," Methods, vol. 36, pp. 25-34 (2005).
Kawano, M. et al., "Autocrine generation and requirement of BSF-2/IL-6," Nature, vol. 332, pp. 83-85 (1998).
Kettleborough, C.A. et al., "Isolation of tumor cell-specific single-chain Fv from immunized mice using phage-antibody libraries and the re-construction of whole antibodies from these antibody fragments," Eur. J. Immunol., vol. 24, pp. 952-958 (1994).
Kishimoto, T. et al., "Interleukin-6 family of cytokines and gp130," Blood, vol. 86, No. 4, pp. 1243-1254 (1995).
Kishimoto, T., "Interleukin-6: from basic science to medicine-40 years in immunology," Annu. Rev. Immunol., vol. 23, pp. 1-21 (2005).
Köhler, G. et al., "Continuous cultures of fused cells secreting antibody of predefined specificity," Nature, vol. 256, pp. 495-497 (1975).
Kozbor, D. et al., "The production of monoclonal antibodies from human lymphocytes," Immunology Today, vol. 4, pp. 72-79 (1983).

(56) References Cited

OTHER PUBLICATIONS

Low, N.M. et al., "Mimicking somatic hypermutation: affinity maturation of antibodies displayed on bacteriophage using a bacterial mutator strain," J. Mol. Biol., vol. 250, pp. 359-368 (1996).

MacCullum, et al., "Antibody-antigen interactions: Contact Analysis and Binding Site Topography," Journal of Molecular Biology, vol. 262, No. 5, pp. 732-745 (1996).

Marks, J.D. et al., "By-passing immunization: building high affinity human antibodies by chain shuffling," Bio/Technology, vol. 10, pp. 779-783 (1992).

Matsuda, T. et al, "Establishment of an interleukin (IL6)/B cell stimulatory factor 2-dependent cell line and preparation of anti-IL6 monoclonal antibodies," Eur. J. Immunol., vol. 18, pp. 951-956 (1988).

Mihara, M. et al., "IL-6 receptor blockage inhibits the onset of autoimmune kidney disease in NZB/WF$_1$," Clin. Exp. Immunol., vol. 112, pp. 397-402 (1998).

Muhandiram, D.R. et al., "Gradient-enhanced triple-resonance three-dimensional NMR experiments with improved sensitivity," J. Magn. Reson, Series B 103, No. 3, pp. 203-216 (1994).

Muskett, F.W. et al., "High resolution structure of the N-terminal domain of tissue inhibitor of metalloproteinases-2 and characterization of its interaction site with matrix metalloproteinase-3," J. Biol. Chem., vol. 273, No. 34, pp. 21736-21743 (1998).

Noma, T. et al., "Enhancement of the interleukin 2 receptor expression on T cells by multiple B-lymphotropic lymphokines," Immunol. Letts., vol. 15, pp. 249-253 (1987).

Okada, M. et al., "IL-6/BSF-2 functions as a killer helper factor in the in vitro induction of cytotoxic T cells," J. Immunol., vol. 141, No. 5, pp. 1543-1549 (1998).

Padlan, et al., "Structure of an antibody-antigen complex: Crystal structure of the HyHEL-10 Fab-lysozyme complex", Proc. Natl. Acad. Sci. USA, vol. 86, pp. 5938-5942 (1989).

Patten, P.A. et al., "Applications of DNA shuffling to pharmaceuticals and vaccines," Curr. Opin. Biotechnol., vol. 8, pp. 724-733 (1997).

Paul, W.E., Fundamental Immunology, Ed. 3, Chapter 9, pp. 292-295, under the heading "Fv Structure and Diversity in Three Dimensions" (1993).

Persic, L. et al., "An integrated vector system for the eukaryotic expression of antibodies or their fragments after selection from phage display libraries," Gene, vol. 187, pp. 9-18 (1997).

Rathanaswami, P. et al., "Demonstration of an in vivo generated sub-picomolar affinity fully human monoclonal antibody to interleukin-8," Biochem. Biophys. Res. Comm., vol. 334, No. 4, pp. 1004-1013 (2005).

Ravetch, J.V. et al., "Structure of the human immunoglobulin μ locus: characterization of embryonic and rearranged J and D genes," Cell, vol. 27, 583-591 (1981).

Razai, A., et al., "Molecular evolution of antibody affinity for sensitive detection of botulinum neurotoxin type A", J. Mol. Biol., vol. 351, No. 1, pp. 158-169 (2005).

Reichmann, L. et al., "Reshaping human antibodies for therapy," Nature, vol. 332, pp. 323-324 (1998).

Salzmann, M. et al., "Trosy in triple-resonance experiments: new perspectives for sequential NMR assignment of large proteins," Proc. Natl. Acad. Sci. USA, vol. 95, pp. 13585-13590 (1998).

Sato, K. et al., "Humanization of an anti-human IL-6 mouse monoclonal antibody glycosylated in its heavy chain variable region", Human Antibodies and Hybridomas, vol. 7, No. 4, pp. 175-183 (1996).

Thompson, J. et al., "Affinity maturation of a high-affinity human monoclonal antibody against the third hypervariable loop of human immunodeficiency virus: use of phage display to improve affinity and broaden strain reactivity," J. Mol. Biol., vol. 256, pp. 77-88 (1996).

Thorpe, P.E. et al., "The preparation and cytotoxic properties of antibody-toxin conjugates," Immunol. Rev., vol. 62, pp. 119-158 (1982).

Vaughan, T.J. et al., "Human antibodies by design," Nature Biotechnology, vol. 16, pp. 535-539 (1998).

Verma, R. et al., "Antibody engineering: comparison of bacterial, yeast, insect and mammalian expression systems," J. of Immunological Methods, vol. 216, pp. 165-181 (1998).

Wendling, D. et al., "Treatment of severe rheumatoid arthritis by anti-interleukin 6 monoclonal antibody," J. of Rheumatology, vol. 20, pp. 259-262 (1993).

Whittle, N. et al., "Expression in COS cells of a mouse—human chimaeric B72.3 antibody," Protein Eng., vol. 1, No. 6, pp. 499-505 (1987).

Wittekind, M. et al., "HNCACB, a high-sensitivity 3D NMR experiment to correlate amide-proton and nitrogen resonances with the alpha- and beta-carbon resonances in proteins," J. Magn. Reson., Series B 101, No. 2, pp. 201-205 (1993).

Xu, G.Y. et al., "Solution structure of recombinant human interleukin-6," J. Mol. Biol., vol. 268, pp. 468-481 (1997).

Yamamoto, M. et al., "IL-6 required for the development of Th1 cell-mediated murine colitis," J. of Immunology, vol. 164, pp. 4878-4882 (2000).

Yang, W.P. et al., "CDR walking mutagenesis for the affinity maturation of a potent human anti-HIV-1 antibody into the picomolar range," J. Mol. Biol., vol. 354, pp. 392-403 (1995).

Zahnd, C., et al., "Directed in Vitro evolution and crystallographic analysis of a peptide-binding single chain antibody fragment (scFv) with low picomolar affinity", J. of Biol. Chem., vol. 279, No. 18, pp. 18870-18877 (2004).

\* cited by examiner

```
            1   5    10   15   20   25   30   35   40   45   50 a  55   60   65   70   75   80 abc 85   90   95  100        105 110
132E09      EVQILETGGGLVKPGGSLRLSCATSGFNFNDYFMNWVRQAPGKGLEWLAQMRNKNYQYGTYYAESLEGRVTVSRDDAKNSVYLQVSSLRAEDTAIYYCTRESYYGFTSYWGQGVMTVSS 3-72        EVQLVESGGGLVQPGGSLRLSCAASGFTFSDHYMDWVRQAPGKGLEWVGRFTISRDNSKNTLYLQMNSLKTEDTAVYYCAR                      YFDYWGQGTLVTVSS gH13        EVQLVESGGGLVQPGGSLRLSCAASGFNFNDYFMNWVRQAPGKGLEWVAQMRNKNYQYGTYYAESLEGRFTISRDDSKNSLYLQMNSLKTEDTAVYYCARESYYGFTSYWGQGTLVTVSS
```

(b)

```
            1   5   10   15   20   25   30   35   40   45   50   55   60   65   70   75   80   85   90   95  100  105
132E09      DIQMTQSPASLSASLEEIVTITCCQASQDIGISLSWYQQKPGRTPQLLIQNANNLADGVPSRFSGRFGTQFSLTISTPQVEDFGVYYCLQHNSAPYTFGTGTQLEIKR 2-1-(1)O12  DIQMTQSPSSLSASVGDRVTITCRASQSISSYLNWYQQKPGKAPKLLIYAASSLQSGVPSRFSGSGSGTDFTLTISSLQPEDFATYYCQQSYSTPYTFGQGTKLEIKR gL10        DIQMTQSPSSLSASVGDRVTITCCQASQDIGISLSWYQQKPGKAPKLLIYNANNLADGVPSRFSGSGSGTDFTLTISSLQPEDFATYYCLQHNSAPYTFGQGTKLEIKR
```

Figure 2

(a) Translated sequence of 240.g1 heavy chain, showing intron/exon boundaries

```
                10          20          30          40          50
ATG GAG TGG AGC TGG GTG TTT TTG TTC TTC CTG TCC GTG ACC ACA GGC GTG CAC TCT
TAC CTC ACC TCG ACC CAC AAA AAC AAG AAG GAC AGG CAC TGG TGT CCG CAC GTG AGA
 M   E   W   S   W   V   F   L   F   F   L   S   V   T   T   G   V   H   S>

60          70          80          90         100         110
GAA GTC CAG CTC GTT GAG AGT GGC GGT GGC CTG GTC CAG CCC GGT GGA TCA CTC CGA
CTT CAG GTC GAG CAA CTC TCA CCG CCA CCG GAC CAG GTC GGG CCA CCT AGT GAG GCT
 E   V   Q   L   V   E   S   G   G   G   L   V   Q   P   G   G   S   L   R>

120         130         140         150         160         170
CTG TCC TGC GCT GCA AGC GGG TTT AAT TTT AAT GAT TAC TTC ATG AAC TGG GTT CGG
GAC AGG ACG CGA CGT TCG CCC AAA TTA AAA TTA CTA ATG AAG TAC TTG ACC CAA GCC
 L   S   C   A   A   S   G   F   N   F   N   D   Y   F   M   N   W   V   R>

180         190         200         210         220
CAG GCA CCT GGC AAA GGC CTG GAA TGG GTG GCT CAG ATG AGG AAC AAG AAT TAT CAG
GTC CGT GGA CCG TTT CCG GAC CTT ACC CAC CGA GTC TAC TCC TTG TTC TTA ATA GTC
 Q   A   P   G   K   G   L   E   W   V   A   Q   M   R   N   K   N   Y   Q>

230         240         250         260         270         280
TAC GGG ACA TAC TAT GCC GAG AGT CTG GAG GGA AGG TTC ACC ATC TCC AGG GAC GAT
ATG CCC TGT ATG ATA CGG CTC TCA GAC CTC CCT TCC AAG TGG TAG AGG TCC CTG CTA
 Y   G   T   Y   Y   A   E   S   L   E   G   R   F   T   I   S   R   D   D>

290         300         310         320         330         340
TCT AAG AAC AGC CTC TAC CTT CAG ATG AAC TCT TTG AAA ACC GAG GAC ACA GCC GTG
AGA TTC TTG TCG GAG ATG GAA GTC TAC TTG AGA AAC TTT TGG CTC CTG TGT CGG CAC
 S   K   N   S   L   Y   L   Q   M   N   S   L   K   T   E   D   T   A   V>

350         360         370         380         390
TAC TAT TGT GCT AGA GAA AGT TAT TAC GGG TTC ACA TCT TAT TGG GGA CAG GGA ACC
ATG ATA ACA CGA TCT CTT TCA ATA ATG CCC AAG TGT AGA ATA ACC CCT GTC CCT TGG
 Y   Y   C   A   R   E   S   Y   Y   G   F   T   S   Y   W   G   Q   G   T>

400         410         420         430         440         450
CTG GTG ACT GTC TCG AGC GCT TCT ACA AAG GCC CCA TCC GTC TTC CCC CTG GCG CCC
GAC CAC TGA CAG AGC TCG CGA AGA TGT TTC CGG GGT AGG CAG AAG GGG GAC CGC GGG
 L   V   T   V   S   S   A   S   T   K   G   P   S   V   F   P   L   A   P>

460         470         480         490         500         510
TGC TCC AGG AGC ACC TCC GAG AGC ACA GCC GCC CTG GGC TGC CTG GTC AAG GAC TAC
ACG AGG TCC TCG TGG AGG CTC TCG TGT CGG CGG GAC CCG ACG GAC CAG TTC CTG ATG
 C   S   R   S   T   S   E   S   T   A   A   L   G   C   L   V   K   D   Y>
```

Fig. 2(a)(cont.)

```
        520         530         540         550         560         570
TTC CCC GAA CCG GTG ACG GTG TCG TGG AAC TCA GGC GCC CTG ACC AGC GGC GTG CAC
AAG GGG CTT GGC CAC TGC CAC AGC ACC TTG AGT CCG CGG GAC TGG TCG CCG CAC GTG
 F   P   E   P   V   T   V   S   W   N   S   G   A   L   T   S   G   V   H>

580         590         600         610         620
ACC TTC CCG GCT GTC CTA CAG TCC TCA GGA CTC TAC TCC CTC AGC AGC GTG GTG ACC
TGG AAG GGC CGA CAG GAT GTC AGG AGT CCT GAG ATG AGG GAG TCG TCG CAC CAC TGG
 T   F   P   A   V   L   Q   S   S   G   L   Y   S   L   S   S   V   V   T>

630         640         650         660         670         680
GTG CCC TCC AGC AGC TTG GGC ACG AAG ACC TAC ACC TGC AAC GTA GAT CAC AAG CCC
CAC GGG AGG TCG TCG AAC CCG TGC TTC TGG ATG TGG ACG TTG CAT CTA GTG TTC GGG
 V   P   S   S   S   L   G   T   K   T   Y   T   C   N   V   D   H   K   P>

690         700         710    ↓    720         730         740         750
AGC AAC ACC AAG GTG GAC AAG AGA GTT G GTGAGAGGCCAGCACAGGGAGGGAGGGTGTCTGCTGGA
TCG TTG TGG TTC CAC CTG TTC TCT CAA C CACTCTCCGGTCGTGTCCCTCCCTCCCACAGACGACCT
 S   N   T   K   V   D   K   R   V>

760         770         780         790         800         810         820
AGCCAGGCTCAGCCCTCCTGCCTGGACGCACCCCGGCTGTGCAGCCCCAGCCCAGGGCAGCAAGGCATGCCCCAT
TCGGTCCGAGTCGGGAGGACGGACCTGCGTGGGGCCGACACGTCGGGGTCGGGTCCCGTCGTTCCGTACGGGGTA 830         840         850         860         870         880         890         900
CTGTCTCCTCACCCGGAGGCCTCTGACCACCCCACTCATGCCCAGGGAGAGGGTCTTCTGGATTTTTCCACCAGG
GACAGAGGAGTGGGCCTCCGGAGACTGGTGGGGTGAGTACGGGTCCCTCTCCCAGAAGACCTAAAAAGGTGGTCC 910         920         930         940         950         960         970
CTCCGGGCAGCCACAGGCTGGATGCCCCTACCCCAGGCCCTGCGCATACAGGGGCAGGTGCTGCGCTCAGACCTG
GAGGCCCGTCGGTGTCCGACCTACGGGGATGGGGTCCGGGACGCGTATGTCCCCGTCCACGACGCGAGTCTGGAC 980         990        1000        1010        1020        1030        1040        1050
CCAAGAGCCATATCCGGGAGGACCCTGCCCCTGACCTAAGCCCACCCCAAAGGCCAAACTCTCCACTCCCTCAGC
GGTTCTCGGTATAGGCCCTCCTGGGACGGGGACTGGATTCGGGTGGGGTTTCCGGTTTGAGAGGTGAGGGAGTCG 1060        1070        1080        1090        1100    ↓   1110
TCAGACACCTTCTCTCCTCCCAGATCTGAGTAACTCCCAATCTTCTCTCTGCAG AG TCC AAA TAT GGT
AGTCTGTGGAAGAGAGGAGGGTCTAGACTCATTGAGGGTTAGAAGAGAGACGTC TC AGG TTT ATA CCA
                                                         E   S   K   Y   G>

1120        1130        1140 ↓
CCC CCA TGC CCA CCA TGC CCA G
GGG GGT ACG GGT GGT ACG GGT C
 P   P   C   P   P   C   P>

1150        1160        1170        1180        1190        1200
GTAAGCCAACCCAGGCCTCGCCCTCCAGCTCAAGGCGGGACAGGTGCCCTAGAGTAGCCT
```

Fig. 2(a)(cont.)

```
CATTCGGTTGGGTCCGGAGCGGGAGGTCGAGTTCCGCCCTGTCCACGGGATCTCATCGGA 1210      1220      1230      1240      1250          ↓
GCATCCAGGGACAGGCCCCAGCCGGGTGCTGACGCATCCACCTCCATCTCTTCCTCAG CA CCT GAG TTC
CGTAGGTCCCTGTCCGGGGTCGGCCCACGACTGCGTAGGTGGAGGTAGAGAAGGAGTC GT GGA CTC AAG
                                                             A   P   E   F>

1270        1280        1290        1300        1310        1320
    CTG GGG GGA CCA TCA GTC TTC CTG TTC CCC CCA AAA CCC AAG GAC ACT CTC ATG ATC
    GAC CCC CCT GGT AGT CAG AAG GAC AAG GGG GGT TTT GGG TTC CTG TGA GAG TAC TAG
     L   G   G   P   S   V   F   L   F   P   P   K   P   K   D   T   L   M   I>

1330        1340        1350        1360        1370        1380
        TCC CGG ACC CCT GAG GTC ACG TGC GTG GTG GTG GAC GTG AGC CAG GAA GAC CCC GAG
        AGG GCC TGG GGA CTC CAG TGC ACG CAC CAC CAC CTG CAC TCG GTC CTT CTG GGG CTC
         S   R   T   P   E   V   T   C   V   V   V   D   V   S   Q   E   D   P   E>

1390        1400        1410        1420        1430        1440
            GTC CAG TTC AAC TGG TAC GTG GAT GGC GTG GAG GTG CAT AAT GCC AAG ACA AAG CCG
            CAG GTC AAG TTG ACC ATG CAC CTA CCG CAC CTC CAC GTA TTA CGG TTC TGT TTC GGC
             V   Q   F   N   W   Y   V   D   G   V   E   V   H   N   A   K   T   K   P>

1450        1460        1470        1480        1490
                CGG GAG GAG CAG TTC AAC AGC ACG TAC CGT GTG GTC AGC GTC CTC ACC GTC CTG CAC
                GCC CTC CTC GTC AAG TTG TCG TGC ATG GCA CAC CAG TCG CAG GAG TGG CAG GAC GTG
                 R   E   E   Q   F   N   S   T   Y   R   V   V   S   V   L   T   V   L   H>

1500        1510        1520        1530        1540        1550
    CAG GAC TGG CTG AAC GGC AAG GAG TAC AAG TGC AAG GTC TCC AAC AAA GGC CTC CCG
    GTC CTG ACC GAC TTG CCG TTC CTC ATG TTC ACG TTC CAG AGG TTG TTT CCG GAG GGC
     Q   D   W   L   N   G   K   E   Y   K   C   K   V   S   N   K   G   L   P>

1560        1570        1580            ↓
        TCC TCC ATC GAG AAA ACC ATC TCC AAA GCC AAA G
        AGG AGG TAG CTC TTT TGG TAG AGG TTT CGG TTT C
         S   S   I   E   K   T   I   S   K   A   K>

1590      1600      1610      1620      1630      1640      1650
GTGGGACCCACGGGGTGCGAGGGCCACATGGACAGAGGTCAGCTCGGCCCACCCTCTGCCCT
CACCCTGGGTGCCCCACGCTCCCGGTGTACCTGTCTCCAGTCGAGCCGGGTGGGAGACGGGA 1660      1670      1680    ↓ 1690      1700      1710
GGGAGTGACCGCTGTGCCAACCTCTGTCCCTACAG GG CAG CCC CGA GAG CCA CAG GTG TAC ACC
CCCTCACTGGCGACACGGTTGGAGACAGGGATGTC CC GTC GGG GCT CTC GGT GTC CAC ATG TGG
                                     G   Q   P   R   E   P   Q   V   Y   T>

1720        1730        1740        1750        1760        1770
    CTG CCC CCA TCC CAG GAG GAG ATG ACC AAG AAC CAG GTC AGC CTG ACC TGC CTG GTC
    GAC GGG GGT AGG GTC CTC CTC TAC TGG TTC TTG GTC CAG TCG GAC TGG ACG GAC CAG
```

Fig. 2(a)(cont.)
And
Fig. 2(b)

```
              L     P     P     S     Q     E     E     M     T     K     N     Q     V     S     L     T     C     L     V>
                      1780            1790            1800            1810            1820
             AAA   GGC   TTC   TAC   CCC   AGC   GAC   ATC   GCC   GTG   GAG   TGG   GAG   AGC   AAT   GGG   CAG   CCG   GAG
             TTT   CCG   AAG   ATG   GGG   TCG   CTG   TAG   CGG   CAC   CTC   ACC   CTC   TCG   TTA   CCC   GTC   GGC   CTC
              K     G     F     Y     P     S     D     I     A     V     E     W     E     S     N     G     Q     P     E>

1830            1840            1850            1860            1870            1880
       AAC   AAC   TAC   AAG   ACC   ACG   CCT   CCC   GTG   CTG   GAC   TCC   GAC   GGC   TCC   TTC   TTC   CTC   TAC
       TTG   TTG   ATG   TTC   TGG   TGC   GGA   GGG   CAC   GAC   CTG   AGG   CTG   CCG   AGG   AAG   AAG   GAG   ATG
        N     N     Y     K     T     T     P     P     V     L     D     S     D     G     S     F     F     L     Y>

1890            1900            1910            1920            1930            1940
       AGC   AGG   CTA   ACC   GTG   GAC   AAG   AGC   AGG   TGG   CAG   GAG   GGG   AAT   GTC   TTC   TCA   TGC   TCC
       TCG   TCC   GAT   TGG   CAC   CTG   TTC   TCG   TCC   ACC   GTC   CTC   CCC   TTA   CAG   AAG   AGT   ACG   AGG
        S     R     L     T     V     D     K     S     R     W     Q     E     G     N     V     F     S     C     S>

1950            1960            1970            1980            1990
             GTG   ATG   CAT   GAG   GCT   CTG   CAC   AAC   CAC   TAC   ACA   CAG   AAG   AGC   CTC   TCC   CTG   TCT   CTG
             CAC   TAC   GTA   CTC   CGA   GAC   GTG   TTG   GTG   ATG   TGT   GTC   TTC   TCG   GAG   AGG   GAC   AGA   GAC
              V     M     H     E     A     L     H     N     H     Y     T     Q     K     S     L     S     L     S     L>

2000
       GGT   AAA   TGA
       CCA   TTT   ACT
        G     K     *>
```

(b) Light chain

```
                  10            20            30            40            50            60
             ATG   AGC   GTG   CCT   ACC   CAG   GTC   CTC   GGC   CTG   TTG   CTG   CTC   TGG   CTG   ACC   GAT   GCC   CGC   TGC   GAT
             TAC   TCG   CAC   GGA   TGG   GTC   CAG   GAG   CCG   GAC   AAC   GAC   GAG   ACC   GAC   TGG   CTA   CGG   GCG   ACG   CTA
              M     S     V     P     T     Q     V     L     G     L     L     L     L     W     L     T     D     A     R     C     D>

70            80            90            100           110           120
             ATC   CAG   ATG   ACT   CAA   TCA   CCC   AGT   TCC   CTG   AGC   GCC   TCT   GTC   GGC   GAC   AGG   GTG   ACC   ATC   ACA
             TAG   GTC   TAC   TGA   GTT   AGT   GGG   TCA   AGG   GAC   TCG   CGG   AGA   CAG   CCG   CTG   TCC   CAC   TGG   TAG   TGT
              I     Q     M     T     Q     S     P     S     S     L     S     A     S     V     G     D     R     V     T     I     T>

130           140           150           160           170           180
             TGC   CAG   GCC   TCT   CAA   GAC   ATT   GGC   ATC   AGC   CTG   TCC   TGG   TAC   CAG   CAA   AAA   CCC   GGC   AAG   GCC
             ACG   GTC   CGG   AGA   GTT   CTG   TAA   CCG   TAG   TCG   GAC   AGG   ACC   ATG   GTC   GTT   TTT   GGG   CCG   TTC   CGG
              C     Q     A     S     Q     D     I     G     I     S     L     S     W     Y     Q     Q     K     P     G     K     A>

190           200           210           220           230           240           250
       CCT   AAG   CTC   CTG   ATC   TAC   AAT   GCT   AAC   AAC   CTG   GCC   GAT   GGC   GTG   CCT   AGT   AGG   TTT   AGC   GGG
       GGA   TTC   GAG   GAC   TAG   ATG   TTA   CGA   TTG   TTG   GAC   CGG   CTA   CCG   CAC   GGA   TCA   TCC   AAA   TCG   CCC
        P     K     L     L     I     Y     N     A     N     N     L     A     D     G     V     P     S     R     F     S     G>
```

Fig. 2(b)(cont.)

```
      260         270         280         290         300         310
TCT GGT TCC GGA ACA GAT TTC ACA CTC ACC ATC AGC TCA CTG CAG CCC GAG GAC TTC GCC ACT
AGA CCA AGG CCT TGT CTA AAG TGT GAG TGG TAG TCG AGT GAC GTC GGG CTC CTG AAG CGG TGA
 S   G   S   G   T   D   F   T   L   T   I   S   S   L   Q   P   E   D   F   A   T>

320         330         340         350         360         370
TAC TAT TGC CTG CAG CAC AAC AGC GCC CCC TAC ACC TTC GGA CAA GGC ACT AAA CTG GAG ATC
ATG ATA ACG GAC GTC GTG TTG TCG CGG GGG ATG TGG AAG CCT GTT CCG TGA TTT GAC CTC TAG
 Y   Y   C   L   Q   H   N   S   A   P   Y   T   F   G   Q   G   T   K   L   E   I>

380         390         400         410         420         430         440
AAG CGT ACG GTA GCG GCC CCA TCT GTC TTC ATC TTC CCG CCA TCT GAT GAG CAG TTG AAA TCT
TTC GCA TGC CAT CGC CGG GGT AGA CAG AAG TAG AAG GGC GGT AGA CTA CTC GTC AAC TTT AGA
 K   R   T   V   A   A   P   S   V   F   I   F   P   P   S   D   E   Q   L   K   S>

450         460         470         480         490         500
GGA ACT GCC TCT GTT GTG TGC CTG CTG AAT AAC TTC TAT CCC AGA GAG GCC AAA GTA CAG TGG
CCT TGA CGG AGA CAA CAC ACG GAC GAC TTA TTG AAG ATA GGG TCT CTC CGG TTT CAT GTC ACC
 G   T   A   S   V   V   C   L   L   N   N   F   Y   P   R   E   A   K   V   Q   W>

510         520         530         540         550         560
AAG GTG GAT AAC GCC CTC CAA TCG GGT AAC TCC CAG GAG AGT GTC ACA GAG CAG GAC AGC AAG
TTC CAC CTA TTG CGG GAG GTT AGC CCA TTG AGG GTC CTC TCA CAG TGT CTC GTC CTG TCG TTC
 K   V   D   N   A   L   Q   S   G   N   S   Q   E   S   V   T   E   Q   D   S   K>

570         580         590         600         610         620         630
GAC AGC ACC TAC AGC CTC AGC AGC ACC CTG ACG CTG AGC AAA GCA GAC TAC GAG AAA CAC AAA
CTG TCG TGG ATG TCG GAG TCG TCG TGG GAC TGC GAC TCG TTT CGT CTG ATG CTC TTT GTG TTT
 D   S   T   Y   S   L   S   S   T   L   T   L   S   K   A   D   Y   E   K   H   K>

640         650         660         670         680         690
GTC TAC GCC TGC GAA GTC ACC CAT CAG GGC CTG AGC TCG CCC GTC ACA AAG AGC TTC AAC AGG
CAG ATG CGG ACG CTT CAG TGG GTA GTC CCG GAC TCG AGC GGG CAG TGT TTC TCG AAG TTG TCC
 V   Y   A   C   E   V   T   H   Q   G   L   S   S   P   V   T   K   S   F   N   R>

700
GGA GAG TGT TAG
CCT CTC ACA ATC
 G   E   C   *>
```

METHODS FOR MAKING ANTIBODY MOLECULES HAVING SPECIFICITY FOR HUMAN IL-6

CROSS REFERENCE TO RELATED APPLICATIONS

The present application is a Continuation of U.S. application Ser. No. 13/288,260, filed on Nov. 3, 2011, now U.S. Pat. No. 8,486,662, which is a Divisional of U.S. application Ser. No. 11/608,408, filed on Dec. 8, 2006, now U.S. Pat. No. 8,075,889, which claims priority under 35 U.S.C. §119(e) to Provisional Application Ser. No. 60/748,926, filed Dec. 9, 2005, each of which are incorporated herein by reference in their entireties.

The present invention relates to antibody molecules having specificity for antigenic determinants of IL-6. The present invention also relates to the therapeutic uses of the antibody molecules and methods for producing the antibody molecules.

IL-6 is a pleiotropic multi-functional cytokine produced by a variety of cell types. It was originally identified as a B-cell differentiation factor (BSF-2) that induced the final maturation of B-cells into antibody producing cells (Hirano et al., 1986 Nature 324, 73-76). IL-6 has been shown to play a central role in immune regulation, inflammation, heamatopoiesis and oncogenesis. Within the immune system, IL-6 induces B-cell antibody production increasing the amount of polyclonal immunoglobulin. It also induces interleukin-2 (IL-2) receptor expression on T-cells (Nomo et al., 1987, Immunol. letters, 15, 3, 249-253) and promotes IL-2 production in activated T-cells thereby inducing both the growth and the differentiation of cytototoxic T-cells (Okada et al., 1988 J Immunol, 141, 5, 1543-1549). IL-6 is also known to determine the differentiation of monocytes into macrophages (Chomarat P et al., 2000 Nature Immunol., 6, 510-514).

The function of IL-6 is not restricted to the immune response as it acts in hematopoiesis, thrombopoiesis, osteoclast formation, elicitation of hepatic acute phase response resulting in the elevation of C-reactive protein (CRP) and serum amyloid A (SAA) protein. It is known to be a growth factor for epidermal keratinocytes, renal mesangial cells, myeloma and plasmacytoma cells (Grossman et al., 1989 Prot Natl Acad. Sci., 86, (16) 6367-6371; Horii et al., 1989, J Immunol, 143, 12, 3949-3955; Kawano et al., 1988, Nature 332, 6159, 83-85). IL-6 is produced by a wide range of cell types including monocytes/macrophages, fibroblasts, epidermal keratinocytes, vascular endothelial cells, renal messangial cells, glial cells, condrocytes, T and B-cells and some tumour cells (Akira et al., 1990, FASEB J., 4, 11, 2860-2867). Except for tumour cells that constitutively produce IL-6, normal cells do not express IL-6 unless appropriately stimulated.

IL-6 is a glycoprotein, a 184 amino acid molecule with a molecular weight of 21 to 28 kD depending on posttranslational modifications. Alternate splice variants are found in some cell types (Kishimoto et al., 1995, Blood, 86, 4, 1243-1254). The IL-6 receptor (IL-6R) complex is comprised of two functionally different membrane proteins, an 80 kD IL-6 specific binding chain (gp80) and a 130 kD signal transduction chain (gp130). Although IL-6 cannot directly bind gp130, it can bind to IL-6R to generate a high-affinity ternary complex of IL-6/IL6R/gp130. The IL-6R binds IL-6 with low affinity, however, IL-6R does not have an intracellular signal transduction domain therefore this ligation alone does not lead to cellular activation. Similarly, cell surface expression of IL-6R does not mean the cell is responsive to IL6 stimulation. Proteolytic cleavage leads to the release of soluble IL-6R (sIL-6R; sgp80) which can bind circulating IL-6 and increase the half-life of IL-6. For cellular activation, IL-6 first binds to either cell bound IL-6R or sIL-6R; the heterodimeric IL-6/IL-6R complex then associates with cell surface glycoprotein gp130. The resulting tripartite heterocomplex binds another 1L-6/1L-6R/gp130 and signal transduction ensues (Bravo and Heath 2000, EMBO J., 19, (11), 2399-2411; Boulanger et al., 2003, Science, 300, 5628, 2101-2104), hence both cell-bound and soluble IL-6R contribute to cellular activation. IL-6 signaling through cell bound IL-6R has been termed cis signaling whilst cellular activation via soluble IL-6R has been described as trans signaling. Cells expressing gp130 but not IL-6R can be stimulated by IL-6 through sIL-6R.

Neutralising murine antibodies to human IL-6 are known to be able to interfere with the binding of human IL-6 to the IL-6R (site 1) or to gp130 (sites 2 and 3) (Kalai et al., 1997, Eur. J. Biochem. 249, 690-700; Brakenhoff et al., 1990, Journal of Immunology, 145, 561-568; Wendling et al., 1993, Journal of Rheumatology, 29, 259-262).

U.S. Pat. No. 5,856,135 discloses reshaped human antibodies to human IL-6 which block IL-6 binding to IL-6R. These antibodies were derived from a mouse monoclonal antibody SK2 in which the complementarity determining regions (CDR's) from the variable region of the mouse antibody SK2 are transplanted into the variable regions of a human antibody.

Also known are neutralising human auto-antibodies to IL-6 (Hansen et al, Eur. J. Immunol, 1995, 25, 348-354).

A site I chimeric murine/human anti-IL-6 antibody was described in WO2004039826 for use in therapy.

A humanised anti-human IL-6 receptor monoclonal antibody is in phase III clinical trials for the treatment of rheumatoid arthritis (Kishimoto, 2005, Annu Rev Immunol. 23:1-21). It has also been reported that the same antibody is efficacious in a phase II study of Crohn's disease. Efficacy has also been demonstrated with both anti-1L-6 and anti-1L-6R antibodies in lupus-like disease in NZB/W F$_l$ mice (Fink et al., 1994 J. Clin. Invest. 94, 585; Mihara et ai., 1998, Clin. Exp. Immunol. 112, 397). A neutralizing antibody to the murine IL-6 receptor suppressed colitis in an adoptive transfer model of disease (Yamamoto et al., 2000 Journal of Immunology, 164, 4878; Atreya et al., 2000 Nature Med 6, 583). The latter study also demonstrated efficacy with an anti-receptor antibody in the IL-10 knock-out mouse model of colitis and in the TNBS model of gut inflammation We have now identified a high affinity neutralising anti-IL-6 antibody that is particularly efficacious in vivo, for example in the in vivo model described herein.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

As used herein, the term 'neutralising antibody' describes an antibody that is capable of neutralising the biological signalling activity of IL-6, for example by blocking the site 3 binding of IL-6 to the gp130 receptor.

Antibodies for use in the present invention may be obtained using any suitable method known in the art. The IL-6 polypeptide or cells expressing the polypeptide can be used to produce antibodies which specifically recognise IL-6. The IL-6 polypeptide may be the 'mature' polypeptide or a biologically active fragment or derivatives thereof. Preferably the IL-6 polypeptide is the mature polypeptide. IL-6 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The IL-6 polypeptide may in some instances be part of a larger protein such as a fusion protein for example fused to an affinity tag. Antibodies generated against the IL-6 polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized. However, mice, rabbits, pigs and rats are generally preferred.

Antibodies for use in the present invention include whole antibodies and functionally active fragments or derivatives thereof and may be, but are not limited to, monoclonal, humanised, fully human or chimeric antibodies.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanised antibodies (which include CDR-grafted antibodies) are antibody molecules from non-human species having one or more complementarity determining regions (CDRs) from the non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are those antibodies encoded by immunoglobulin genes that have been genetically engineered so that the light and heavy chain genes are composed of immunoglobulin gene segments belonging to different species.

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant part genes have been replaced by their human counterparts e.g. as described in general terms in EP0546073 B1, U.S. Pat. No. 5,545,806, U.S. Pat. No. 5,569, 825, U.S. Pat. No. 5,625,126, U.S. Pat. No. 5,633,425, U.S. Pat. No. 5,661,016, U.S. Pat. No. 5,770,429, EP 0438474 B1 and EP0463151 B1.

In one embodiment the present invention provides a neutralising antibody having specificity for human IL-6, comprising a heavy chain, wherein the variable domain of the heavy chain comprises at least one of a CDR having the sequence given in SEQ ID NO:5 for CDR-H1, a CDR having the sequence given in SEQ ID NO:6 for CDR-H2 and a CDR having the sequence given in SEQ ID NO:7 for CDR-H3.

In another embodiment the present invention provides a neutralising antibody having specificity for human IL-6, comprising a heavy chain, wherein at least two of CDR-H1, CDR-H2 and CDR-H3 of the variable domain of the heavy chain are selected from the following: the sequence given in SEQ ID NO:5 for CDR-H1, the sequence given in SEQ ID NO:6 for CDR-H2 and the sequence given in SEQ ID NO:7 for CDR-H3. For example, the antibody may comprise a heavy chain wherein CDR-H1 has the sequence given in SEQ ID NO:5 and CDR-H2 has the sequence given in SEQ ID NO:6. Alternatively, the antibody may comprise a heavy chain wherein CDR-H1 has the sequence given in SEQ ID NO:5 and CDR-H3 has the sequence given in SEQ ID NO:7, or the antibody may comprise a heavy chain wherein CDR-H2 has the sequence given in SEQ ID NO:6 and CDR-H3 has the sequence given in SEQ ID NO:7. For the avoidance of doubt, it is understood that all permutations are included.

In another embodiment the present invention provides a neutralising antibody having specificity for human IL-6, comprising a heavy chain, wherein the variable domain of the heavy chain comprises the sequence given in SEQ ID NO:5 for CDR-H1, the sequence given in SEQ ID NO:6 for CDR-H2 and the sequence given in SEQ ID NO:7 for CDR-H3.

In one embodiment the present invention provides a neutralising antibody having specificity for human IL-6, comprising a light chain, wherein the variable domain of the light chain comprises at least one of a CDR having the sequence given in SEQ ID NO:8 for CDR-L1, a CDR having the sequence given in SEQ ID NO:9 for CDR-L2 and a CDR having the sequence given in SEQ ID NO: 10 for CDR-L3.

In another embodiment the present invention provides a neutralising antibody having specificity for human IL-6, comprising a light chain, wherein at least two of CDR-L1, CDR-L2 and CDR-L3 of the variable domain of the light chain are selected from the following: the sequence given in SEQ ID NO:8 for CDR-L1, the sequence given in SEQ ID NO:9 for CDRL2 and the sequence given in SEQ ID NO:10 for CDR-L3. For example, the antibody may comprise a light chain wherein CDR-L1 has the sequence given in SEQ ID NO:8 and CDR-L2 has the sequence given in SEQ ID NO:9. Alternatively, the antibody may comprise a light chain wherein CDR-L1 has the sequence given in SEQ ID NO:8 and CDR-L3 has the sequence given in SEQ ID NO:10, or the antibody may comprise a light chain wherein CDR-L2 has the sequence given in SEQ ID NO:9 and CDR-L3 has the sequence given in SEQ ID NO:10. For the avoidance of doubt, it is understood that all permutations are included.

In another embodiment the present invention provides a neutralising antibody having specificity for human IL-6, comprising a light chain, wherein the variable domain comprises the sequence given in SEQ ID NO:8 for CDR-L1, the sequence given in SEQ ID NO:9 for CDR-L2 and the sequence given in SEQ ID NO: 10 for CDR-L3.

It will be appreciated that one or more amino acid substitutions, additions and/or deletions may be made to the CDRs provided by the present invention without significantly altering the ability of the antibody to bind to IL-6 and to neutralise IL-6 activity. The effect of any amino acid substitutions, additions and/or deletions can be readily tested by one skilled in the art, for example by using the methods described in the Examples to determine IL-6 binding and neutralisation. Accordingly, in one example the present invention provides an antibody having specificity for human IL-6 comprising one or more CDRs selected from CDRH-1 (SEQ ID NO:5), CDRH-2 (SEQ ID NO:6), CDRH-3 (SEQ ID NO:7), CDRL-1 (SEQ ID NO:8), CDRL-2 (SEQ ID NO:9) and CDRL-3 (SEQ ID NO:10) in which one or more amino acids in one or more of the CDRs has been substituted with another amino acid.

The antibody molecules of the present invention preferably comprise a complementary light chain or a complementary heavy chain, respectively.

Hence in one embodiment, an antibody according to the present invention comprises a heavy chain, wherein the variable domain of the heavy chain comprises the sequence given in SEQ ID NO:5 for CDR-H1, the sequence given in SEQ ID NO:6 for CDR-H2 and the sequence given in SEQ ID NO:7 for CDR-H3 and a light chain wherein the variable domain of the light chain comprises the sequence given in SEQ ID NO:8 for CDR-L1, the sequence given in SEQ ID NO:9 for CDR-L2 and the sequence given in SEQ ID NO:10 for CDR-L3.

In one example the present invention provides an antibody having specificity for human IL-6, comprising a heavy chain, wherein the variable domain of the heavy chain comprises the sequence given in SEQ ID NO:5 for CDR-H1, the sequence given in SEQ ID NO:6 for CDRH-2 and the sequence given in SEQ ID NO:7 for CDRH-3 and a light chain wherein the variable domain of the light chain comprises the sequence given in SEQ ID NO:8 for CDR-L1, the sequence given in SEQ ID NO:9 for CDR-L2 and the sequence given in SEQ ID NO:10 for CDR-L3 in which one or more amino acids in one or more of the CDRs has been substituted with another amino acid.

In one embodiment, an antibody of the present invention comprises a heavy chain, wherein the variable domain of the heavy chain comprises the sequence given in SEQ ID NO:2.

In another embodiment, an antibody of the present invention comprises a heavy chain, wherein the variable domain of the heavy chain comprises a sequence having at least 60% identity or similarity to the sequence given in SEQ ID NO:2. In one embodiment, an antibody of the present invention comprises a heavy chain, wherein the variable domain of the heavy chain comprises a sequence having at least 70%, 80%, 90%, 95% or 98% identity or similarity to the sequence given in SEQ ID NO:2.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, an antibody of the present invention comprises a light chain, wherein the variable domain of the light chain comprises the sequence given in SEQ ID NO:4.

In another embodiment, an antibody of the present invention comprises a light chain, wherein the variable domain of the light chain comprises a sequence having at least 60% identity or similarity to the sequence given in SEQ ID NO:4. In one embodiment the antibody of the present invention comprises a light chain, wherein the variable domain of the light chain comprises a sequence having at least 70%, 80%, 90%, 95% or 98% identity or similarity to the sequence given in SEQ ID NO:4.

In one embodiment an antibody of the present invention comprises a heavy chain, wherein the variable domain of the heavy chain comprises the sequence given in SEQ ID NO:2 and a light chain, wherein the variable domain of the light chain comprises the sequence given in SEQ ID NO:4.

In another embodiment of the invention, the antibody comprises a heavy chain and a light chain, wherein the variable domain of the heavy chain comprises a sequence having at least 60% identity or similarity to the sequence given in SEQ ID NO:2 and the variable domain of the light chain comprises a sequence having at least 60% identity or similarity to the sequence given in SEQ ID NO:4. Preferably, the antibody comprises a heavy chain, wherein the variable domain of the light chain comprises a sequence having at least 70%, 80%, 90%, 95% or 98% identity or similarity to the sequence given in SEQ ID NO:2 and a light chain, wherein the variable domain of the light chain comprises a sequence having at least 70%, 80%, 90%, 95')/0 or 98% identity or similarity to the sequence given in SEQ ID NO:4.

In one embodiment an antibody of the present invention is a rat antibody, in which the variable domain of the heavy chain comprises the sequence given in SEQ ID NO:2, and the variable domain of the light chain comprises the sequence given in SEQ ID NO:4. This rat antibody is referred to herein as '132E09' or as the "donor" antibody. The complete nucleotide and amino acid sequence of the variable domain of the heavy chain of rat antibody 132E09 are provided in SEQ ID NOS: 1 and 2 respectively. The complete nucleotide and amino acid sequence of the variable domain of the light chain of rat antibody 132E09 are provided in SEQ ID NOS: 3 and 4 respectively. The CDRs given in SEQ ID NOS: 5, 6, 7, 8, 9 and 10 are derived from the rat antibody 132E09.

In one embodiment an antibody of the present invention is a CDR-grafted antibody. As used herein, the term 'CDR-grafted antibody' refers to an antibody wherein the heavy and/or light chain contains one or more CDRs (including, if desired, one or more modified CDRs) from a donor antibody (e.g. a rat antibody) grafted into a heavy and/or light chain variable region framework of an acceptor antibody (e.g. a human antibody). For a review, see Vaughan et al, Nature Biotechnology, 16, 535-539, 1998. Preferably one or more of the CDRs have been obtained from the rat antibody 132E09 (SEQ ID NOS:5, 6, 7, 8, 9 and 10). In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including rat, mouse, primate and human framework regions. Preferably, the CDR-grafted antibody of the present invention has at least one variable domain comprising human acceptor framework regions as well as one or more of the CDRs derived from the donor antibody as referred to above. Thus, provided is a neutralising CDR-grafted antibody wherein the variable domain comprises human acceptor framework regions and non-human, preferably rat, donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; the sequences of these are available on the internet at vbase.mrc-cpe.cam.ac.uk.

In a CDR-grafted antibody of the present invention, the acceptor heavy and light chains do not necessarily need to be derived from the same antibody and may, if desired, comprise composite chains having framework regions derived from different chains.

The preferred framework region for the heavy chain of the CDR-grafted antibody of the present invention is derived from the human sub-group VH3 sequence 1-4 3-72 together with JH4 (shown in FIG. 1a; SEQ ID NOS: 19 and 20). Accordingly, provided is a neutralising CDR-grafted antibody comprising at least one non-human donor CDR wherein the heavy chain framework region is derived from the human subgroup sequence 1-4 3-72 together with JH4. The sequence of human JH4 is as follows: (YFDY)WGQGTLVTVSS (SEQ ID NO:20). The YFDY motif is part of CDR-H3 and is not part of framework 4 (Ravetch, J V. et al., 1981, Cell, 27, 583-591). The donor sequence is the 132E09 VH sequence (SEQ ID NO:2) shown in FIG. 1a and the donor CDRs (SEQ ID NOs: 5, 6 and 7) are underlined.

The preferred framework region for the light chain of the CDR-grafted antibody of the present invention is derived from the human germline sub-group VK1 sequence 2-1-(1) 012 together with JK2 shown in FIG. 1b (SEQ ID NO: 21 and 22). Accordingly, provided is a neutralising CDR-grafted antibody comprising at least one non-human donor CDR wherein the light chain framework region is derived from the human subgroup sequence VK1 2-1-(1) 012 together with JK2. The JK2 sequence is as follows: (YT)FGQGTKLEIKR (SEQ ID NO:22). The YT motif is part of CDR-L3 and is not part of framework 4 (Hieter, P A., et al., 1982, J. Biol. Chem., 257, 1516-1522). The donor sequence is the 132E09 VL sequence (SEQ ID NO:4) shown in FIG. 1b and the donor CDRs (SEQ ID NOs: 8, 9 and 10) are underlined.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has the human VH3 sequence 1-4 3-72 together with JH4, then the acceptor framework regions of the heavy chain comprise, in addition to one or more donor CDRs, a donor residue at at least position 49 (according to Kabat et al., (supra)). Accordingly, provided is a CDR-grafted antibody, wherein at least the residue at position 49 of the variable domain of the heavy chain is a donor residue.

Preferably, in a CDR-grafted antibody molecule according to the present invention, if the acceptor light chain has the human sub-group VK1 sequence 2-1-(1) 012 together with JK2, then no donor residues are used in the acceptor framework regions of the light chain and only one or more donor CDRs are transferred.

Donor residues are residues from the donor antibody, i.e. the antibody from which the CDRs were originally derived, which in the case of the present invention is the rat antibody 132E09.

Accordingly, the present invention provides an antibody in which the heavy chain variable region comprises the sequence of gH13 (FIG. 2; SEQ ID NO: 11).

In one embodiment of the present invention, the antibody comprises a heavy chain, wherein the variable domain of the heavy chain comprises a sequence having at least 60% identity or similarity to the sequence given in SEQ ID NO: 11.

Preferably, the antibody comprises a heavy chain, wherein the variable domain of the heavy chain comprises a sequence having at least 70%, 80%, 90%, 95% or 98% identity or similarity to the sequence given in SEQ ID NO:11.

In addition, the present invention provides an antibody in which the light chain variable region comprises the sequence of gL10 (FIG. 2; SEQ ID NO:13).

In one embodiment of the present invention, the antibody comprises a light chain, wherein the variable domain of the light chain comprises a sequence having at least 60% identity or similarity to the sequence given in SEQ ID NO:13. Preferably, the antibody comprises a light chain, wherein the variable domain of the light chain comprises a sequence having at least 70%, 80%, 90%, 95% or 98% identity or similarity to the sequence given in SEQ ID NO:13.

Preferably a CDR-grafted antibody according to the present invention comprises a heavy chain comprising the sequence of gH13 (SEQ ID NO:11) and a light chain comprising the sequence of gL10 (SEQ ID NO: 13).

In one embodiment of the present invention, the antibody comprises a heavy chain and a light chain, wherein the variable domain of the heavy chain comprises a sequence having at least 60% identity or similarity to the sequence given in SEQ ID NO:11 and the variable domain of the light chain comprises a sequence having at least 60% identity or similarity to the sequence given in SEQ ID NO:13. Preferably, the antibody comprises a heavy chain, wherein the variable domain of the light chain comprises a sequence having at least 70%, 80%, 90%, 95% or 98% identity or similarity to the sequence given in SEQ ID NO:11 and a light chain, wherein the variable domain of the light chain comprises a sequence having at least 70%, 80%, 90%, 95% or 98% identity or similarity to the sequence given in SEQ ID NO:13.

The antibody molecules of the present invention may comprise a complete antibody molecule having full length heavy and light chains or a fragment thereof and may be, but are not limited to Fab, modified Fab, Fab', F(ab')2, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1 126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities or may be monospecific (see for example WO 92/22853 and WO05/113605).

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and TgG4 isotypes may be used when the antibody molecule is intended for therapeutic purposes and antibody effector functions are not required, e.g. for simply blocking IL-6 activity. It will be appreciated that sequence variants of these constant region domains may also be used. For example IgG molecules in which the serine at position 241 has been changed to proline as described in Angal et al., Molecular Immunology, 1993, 30 (1), 105-108 may be used. Particularly preferred is the IgG4 constant domain comprising this change. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995). Accordingly, the C-terminal lysine of the antibody heavy chain of SEQ ID NO: 16 may be absent.

In a preferred embodiment the antibody provided by the present invention is a neutralising antibody having specificity for human IL-6 in which the heavy chain constant region comprises the human IgG4 constant region in which the serine at position 241 has been substituted by proline as described in Angal et al., supra. Accordingly, the present invention provides an antibody in which the heavy chain comprises or consists of the sequence given in SEQ ID NO: 16. Preferably the light chain constant region is cKappa.

In one embodiment the present invention provides an antibody in which the heavy chain comprises or consists of the sequence given in SEQ ID NO:16 and the light chain comprises or consists of the sequence given in SEQ ID NO:18.

In one embodiment of the invention, the antibody comprises a heavy chain, wherein the heavy chain comprises a sequence having at least 60% identity or similarity to the sequence given in SEQ ID NO:16. Preferably, the antibody comprises a heavy chain, wherein the heavy chain comprises a sequence having at least 70%, 80%, 90%, 95% or 98% identity or similarity to the sequence given in SEQ ID NO:16.

In one embodiment of the invention, the antibody comprises a light chain, wherein the light chain comprises a sequence having at least 60% identity or similarity to the sequence given in SEQ ID NO:18. Preferably, the antibody comprises a light chain, wherein the light chain comprises a sequence having at least 70%, 80%, 90%, 95% or 98% identity or similarity to the sequence given in SEQ ID NO:18.

In one embodiment of the invention, the antibody comprises a heavy chain and a light chain, wherein the heavy chain comprises a sequence having at least 60% identity or similarity to the sequence given in SEQ ID NO:16 and the light chain comprises a sequence having at least 60% identity or similarity to the sequence given in SEQ ID NO:18. Preferably, the antibody comprises a heavy chain, wherein the heavy chain comprises a sequence having at least 70%, 80%, 90%, 95% or 98% identity or similarity to the sequence given in SEQ ID NO:16 and a light chain, wherein the light chain comprises a sequence having at least 70%, 80%, 90%, 95% or 98% identity or similarity to the sequence given in SEQ ID NO:18.

Also provided by the present invention is a specific region or epitope of human IL6 which is bound by an antibody according to the present invention, in particular an antibody comprising any one of CDR-H1 (SEQ ID NO:5), CDR-H2 (SEQ ID NO:6), CDR-H3 (SEQ ID NO:7), CDR-L1 (SEQ ID NO:8), CDR-L2 (SEQ ID NO:9) or CDR-L3 (SEQ ID NO:10), for example, antibody 132E09 or antibodies comprising the heavy chain variable region sequence gH13 (SEQ ID NO: 11) and/or the light chain variable region sequence gL10 (SEQ ID NO:13).

This specific region or epitope of the human IL-6 polypeptide can be identified by any suitable epitope mapping method known in the art in combination with any one of the antibodies provided by the present invention. Examples of such methods include screening peptides of varying lengths derived from IL-6 for binding to the antibody of the present invention with the smallest fragment that can specifically bind to the antibody containing the sequence of the epitope recognised by the antibody. The IL-6 peptides may be produced synthetically or by proteolytic digestion of the IL-6 polypeptide. Peptides that bind the antibody can be identified by, for example, mass spectrometric analysis. In another example, NMR spectroscopy can be used to identify the epitope bound by an antibody of the present invention, as described in the Examples herein. Once identified, the epitopic fragment which binds an antibody of the present invention can be used, if required, as an immunogen to obtain additional neutralising antibodies which bind the same epitope.

In one example, the epitope of human IL-6 bound by an antibody of the present invention comprises at least amino acid residues S47, C50, E93, R104, F105, E106, T149, K150, A153, Q156, Q159 and S169 of human IL-6 (numbering of residues according to Boulanger et al., Science, 300, 2101-2104). In one example, the epitope of human IL-6 bound by an antibody of the present invention comprises amino acid residues S47, C50, E93, R104, F105, E106, T149, K150, A153, Q156, Q159 and S169 and one or more residues selected from C44, S53, A58, V96, Q152, Q154, N155, W157, T163, L165, and E172.

In one example, the epitope of human IL-6 bound by an antibody of the present invention comprises amino acid residues C44, S47, C50, S53, A58, E93, V96, R104, F105, E106, T149, K150, Q152, A153, Q154, N155, Q156, W157, Q159, T163, L165, S169 and E172.

In one embodiment the present invention provides a neutralising antibody having specificity for human IL-6 which binds an epitope of mature human IL-6 which comprises amino acid residues S47, C50, E93, R104, F105, E106, T149, K150, A153, Q 156, Q159 and S169.

In one embodiment the present invention provides a neutralising antibody having specificity for human IL-6 which binds an epitope of mature human IL-6 which comprises amino acid residues S47, C50, E93, R104, F105, E106, T149, K150, A153, Q156, Q159 and S169 and one or more residues selected from C44, S53, A58, V96, Q152, Q154, N155, W157, T163, L165, and E172.

In one embodiment the present invention provides a neutralising antibody having specificity for human IL-6 which binds an epitope of mature human IL-6 which comprises amino acid residues C44, S47, C50, S53, A58, E93, V96, R104, F105, E106, T149, K150, Q152, A153, Q154, N155, Q156, W157, Q159, T163, L165, S169 and E172.

It will be appreciated that the residues named above may also be numbered based on the amino acid numbering of the unprocessed precursor of IL-6 (Swiss Prot Accession number P05231). Using this numbering the residues numbered above according to Boulanger et al., supra as C44, S47, C50, S53, A58, E93, V96, R104, F105, E106, T149, K150, Q152, A153, Q154, N155, Q156, W157, Q159, T163, L165, S169 and E172 become C72, S75, C78, S81, A86, E121, V124, R132, F133, E134, T177, K178, Q180, A181, Q182, N183, Q184, W185, Q187, T191, L193, S197 and E200 respectively.

Preferably an antibody of the present invention blocks the binding of the gp130 receptor to site 3 of human IL-6.

Antibodies which cross-block the binding of the antibodies of the present invention to IL-6 may be similarly useful in neutralising IL-6 activity. Accordingly, the present invention also provides a neutralising antibody having specificity for human IL-6, which cross-blocks the binding of any one of the antibodies described above to human IL-6 and/or is cross-blocked from binding IL-6 by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above. In another embodiment the cross-blocking neutralising antibody of this aspect of the invention does not bind to the same epitope as an antibody of the present invention or an epitope that borders and/or overlaps with said epitope.

Cross-blocking antibodies can be identified using any suitable method in the art, for example by using competition ELISA or BIAcore where binding of the cross blocking antibody to human IL-6 prevents the binding of an antibody of the present invention or vice versa.

In one embodiment there is provided a neutralising antibody having specificity for human IL-6, which cross-blocks the binding of antibody 132E09 or an antibody whose heavy chain comprises the sequence gH13 (SEQ ID NO:11) or an antibody whose light chain comprises the sequence gL10 (SEQ ID NO:13) or an antibody comprising any one of CDR-H1 (SEQ ID NO:5), CDR-H2 (SEQ ID NO:6), CDR-H3 (SEQ ID NO:7), CDR-L1 (SEQ ID NO:8), CDR-L2 (SEQ ID NO:9) or CDR-L3 (SEQ ID NO:10) to human IL-6. In one embodiment the cross-blocking antibodies provided by the present invention inhibit the binding of 132E09 or an antibody whose heavy chain comprises the sequence gH13 (SEQ ID NO:11) or an antibody whose light chain comprises the sequence gL10 (SEQ ID NO:13) or an antibody comprising any one of CDR-H1 (SEQ ID NO:5), CDR-H2 (SEQ ID NO:6), CDR-H3 (SEQ ID NO:7), CDR-L1 (SEQ ID NO:8), CDR-L2 (SEQ ID NO:9) or CDR-L3 (SEQ ID NO:10) to human IL-6 by 80% or greater, by 85% or greater, by 90% or greater, or by 95% or greater.

Alternatively or in addition, neutralising antibodies according to this aspect of the invention may be cross-blocked from binding to human IL-6 by any one of the antibodies of the present invention. Also provided therefore is a neutralising antibody molecule having specificity for human IL-6 which is cross-blocked from binding human IL-6 by the antibody 132E09 or an antibody whose heavy chain comprises the sequence gH13 (SEQ ID NO:11) or an antibody whose light chain comprises the sequence gL10 (SEQ ID NO:13) or an antibody comprising any one of CDR-H1 (SEQ ID NO:5), CDR-H2 (SEQ ID NO:6), CDR-H3 (SEQ ID NO:7), CDR-L1 (SEQ ID NO:8), CDR-L2 (SEQ ID NO:9) or CDR-L3 (SEQ ID NO:10). In one embodiment the neutralising antibodies provided by this aspect of the invention are inhibited from binding human TL-6 by 132E09 or an antibody whose heavy chain comprises the sequence gH13 (SEQ ID NO:11) or an antibody whose light chain comprises the sequence gL10 (SEQ ID NO:13) or an antibody comprising any one of CDR-H1 (SEQ ID NO:5), CDR-H2 (SEQ ID NO:6), CDR-H3 (SEQ ID NO:7), CDR-L1 (SEQ ID NO:8), CDR-L2 (SEQ ID NO:9) or CDRL3 (SEQ ID NO:10) by 80% or greater, by 85% or greater, by 90% or greater, or by 95% or greater.

The antibody molecules of the present invention preferably have a high binding affinity for human IL-6, preferably picomolar. Affinity may be measured using any suitable method known in the art, including BIAcore as described in the examples herein. Preferably affinity is measured using recombinant human IL-6 as described in the examples herein. Preferably an antibody molecule according to the present invention has a binding affinity for human IL-6 of less than 500 pM. Preferably an antibody molecule according to the present invention has a binding affinity for human IL-6 of less than 50 pM. Accordingly, in one embodiment an antibody molecule of the present invention has a binding affinity of between about 1 and about 500 pM. In one embodiment the antibody molecule of the present invention has a binding affinity of between about 1 and about 50 pM. Preferably the antibody molecule of the present invention has a binding affinity for human IL-6 of between about 1 and about 20 pM. In one embodiment the antibody of the present invention has a binding affinity for human IL-6 of between 8 and 12 pM. It will be appreciated that the affinity of antibodies provided by the present invention may be altered using any suitable method known in the art. The present invention therefore also relates to variants of the antibody molecules of the present invention, which have an improved affinity for human IL-6. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The antibody molecules of the present invention preferably neutralise IL-6 activity, for example in the in vitro and in vivo assays described in the Examples. In one embodiment these antibodies bind to site 3 of human IL-6.

In one embodiment the present invention provides a neutralising antibody having specificity for human IL-6 which is capable of inhibiting the activity of 0.038 nM human IL-6 by 50% at a concentration of less than 100 pM said inhibitory activity being measured on the IL-6 induced proliferation of T1165 cells. In one embodiment the concentration of antibody which inhibits IL-6 by 50% is less than 50 pM, more preferably less than 20 pM. Preferably the human IL-6 used in the assay is human recombinant IL-6. In one embodiment the neutralising antibody is a humanised or fully human antibody.

In another embodiment the present invention provides a neutralising antibody having specificity for human IL-6 which is capable of inhibiting the activity of 3.84 nM human IL-6 by 50% at a concentration of less than 1 nM said inhibitory activity being measured on the production of MCP-1 by HUVECs in response to human IL-6 and sIL-6R. Preferably the human IL-6 used in the assay is human recombinant IL-6. In one embodiment the neutralising antibody is a humanised or fully human antibody.

If desired an antibody according to the present invention may be conjugated to one or more effector molecule(s). It will be appreciated that in one embodiment the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al, 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, $Lu^{177}$, $Bismuth^{213}$, $Californium^{252}$, $Iridium^{192}$ and $Tungsten^{188}$/$Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an antiangiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule(s) may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984 (published Dec. 15, 2005).

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971). In one example the antibody molecule of the present invention is a modified Fab fragment wherein the modification is the addition to the C-terminal end of its heavy chain one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly(ethyleneglycol)) covalently attached thereto, e.g. according to the methods disclosed in EP 0948544 or EP 1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (cds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides a neutralising antibody molecule having specificity for human IL-6, which is a modified Fab fragment having a heavy chain comprising the sequence given in SEQ ID NO:11 and a light chain comprising the sequence given in SEQ ID NO:13 and having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in SEQ ID NO: 1; SEQ ID NO:3; SEQ ID NO:12; SEQ ID NO:14; SEQ ID NO:15 and SEQ ID NO:17. Nucleotides 1-57 in SEQ ID NO 15 and 1-60 in SEQ ID NO 17 encode the signal peptide sequence from mouse antibody B72.3 (Whittle et al., 1987, Protein Eng. 1(6) 499-505.) which is cleaved to give a neutralising antibody molecule of the present invention. Accordingly the present invention also provides an isolated DNA sequence encoding the heavy chain of an antibody of the present invention which comprises nucleotides 58-2008 of SEQ ID NO:15. The present invention also provides an isolated DNA sequence encoding the light chain of an antibody of the present invention which comprises nucleotides 61-705 of SEQ ID NO:17.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively. Preferably, a vector according to the present invention comprises the sequences given in SEQ ID NOS:15 and 17. Nucleotides 1-57 in SEQ ID NO 15 and 1-60 in SEQ ID NO 17 encode the signal peptide sequence from mouse antibody B72.3 which is most preferably cleaved to give a neutralising antibody molecule of the present invention.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used, see Verma et al., 1998, Journal of Immunological Methods, 216, 165-181. Suitable mammalian host cells include CHO, NSO, myeloma or hybridoma cells. Examples of suitable expression systems include the glutamine synthetase expression system described in WO87/04462.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-10, anti-T cell, anti-IFNγ or anti-LPS antibodies, or non-antibody ingredients such as xanthines.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days or 2 to 30 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammatory diseases. Preferably, the antibody molecule can be used to reduce the inflammatory process or to prevent the inflammatory process.

Also provided is an antibody molecule according to the present invention for use in the treatment and/or prophylaxis of a pathological disorder that is mediated by IL-6 or associated with an increased level of IL-6. The present invention further provides the use of an antibody molecule according to the present invention in the manufacture of a medicament for the treatment and/or prophylaxis of a pathological disorder that is mediated by IL-6 or associated with an increased level of IL-6. Preferably, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, pelvic inflammatory disease, Alzheimer's Disease, Crohn's disease, ulcerative colitis, irritable bowel syndrome, Castleman's disease, ankylosing spondylitis, dermatomyositis, uveitis, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, burns patients, osteoporosis, periodontitis and hypochlorhydia.

Preferably the pathological disorder is rheumatoid arthritis or systemic lupus erythematosus (SLE).

The present invention also provides an antibody molecule according to the present invention for use in the treatment or prophylaxis of pain.

The present invention further provides the use of an antibody molecule according to the present invention in the manufacture of a medicament for the treatment or prophylaxis of pain.

An antibody molecule of the present invention may be utilised in any therapy where it is desired to reduce the effects of IL-6 in the human or animal body. IL-6 may be circulating in the body or may be present in an undesirably high level localised at a particular site in the body, for example a site of inflammation.

An antibody molecule of the present invention is preferably used for the control of inflammatory disease.

The present invention also provides a method of treating human or animal subjects suffering from or at risk of a disorder mediated by IL-6, the method comprising administering to the subject an effective amount of the antibody molecule of the present invention.

The antibody molecule of the present invention may also be used in diagnosis, for example in the in vivo diagnosis and imaging of disease states involving IL-6.

The present invention is further described by way of illustration only in the following examples, which refer to the accompanying Figures, in which:

FIG. 1 shows the graft design for the 240.g1 heavy (FIG. 1a; SEQ ID NOS: 2, 5, 6, 7, 11, 19. and 20) and light chain (FIG. 1b; SEQ ID NOS: 4, 8, 9, 10, 13, 21, 22, and 23) sequences. The symbol (1) highlights differences between donor:acceptor:grafted framework sequences. CDR's are single underlined. These are as defined by Kabat, except for CDR-H1 which encompasses both Kabat and Chothia definitions. Double-underlined sequences are donor framework residues retained in the grafts.

FIG. 2a shows the translated sequence of 240.g1 IgG4 heavy chain, showing intron/exon boundaries. (SEQ ID NOS: 11, 12, 15, 16, and 24).

FIG. 2b shows the translated sequence of 240.g1 light chain, showing intron/exon boundaries. (SEQ ID NOS: 13, 14, 17, 18, and 25).

Figure 4:
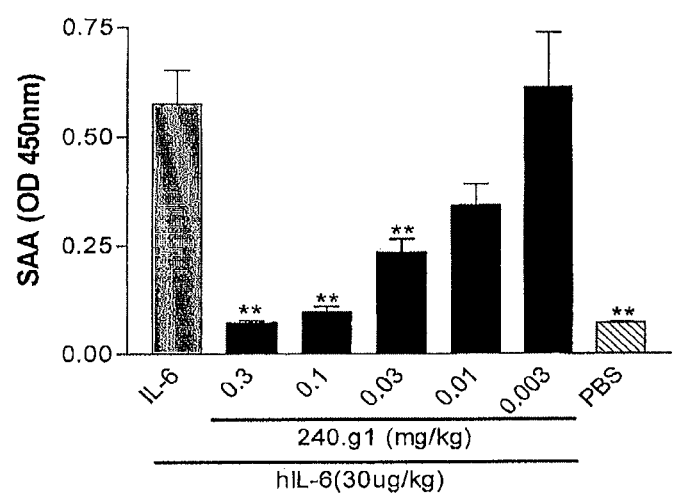

FIG. 4. In vivo neutralisation of hIL-6 induced SAA in mice by administration of CA030_240.g1 (site 3 antibody) n=7-8/group, except PBS n=6. Statistical analysis by ANOVA with Bonferroni post test, ** $P<0.01$ compared with IL-6 alone.

DNA MANIPULATIONS AND GENERAL METHODS

*E. coli* strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from INVITROGEN. Synthetic genes were built at Entelechon. The concentration of Fab and IgG was determined using assembly ELISA.

EXAMPLE 1

Isolation of 132E09

Rats were immunised by subcutaneous injection of recombinant human IL-6 (Peprotech) at three weekly intervals, initially with Freund's Complete Adjuvant and subsequently with Freund's Incomplete Adjuvant. Spleens were harvested one-two weeks after the last immunisation, and single cell suspensions prepared. Immune rat lymphocytes were cultured in the presence of irradiated mouse thymoma EL4 cells and rabbit T cell conditioned media for one week in 96 well microtitre plates. Supernatants were screened for the presence of antibodies specific for human IL-6 in ELISAs. Positives were further screened for the ability to neutralise the biological effects of human IL-6 in a DS1 cell line assay (Bock et al., 1993, Cytokine, 5, 480-489).

Individual B cells secreting antibody with appropriate binding characteristics were isolated from positive microtitre wells according to the Selected Lymphocyte Antibody Method (Babcook et al., 1996, Proc. Natl. Acad. Sci. USA 93, 7843-7848; WO92/02551), and heavy and light chain variable region genes were cloned via reverse transcription PCR from single rat B cells. Variable regions were expressed in recombinant IgG format to confirm binding, and antibody 132E09 was selected for humanisation and further study. The rat variable region sequence was registered as CA030_00240.

The V-region sequences are shown in SEQ ID NOS:1 to 4.

EXAMPLE 2

CDR-Grafting of 132E09

A series of humanised VL and VH regions were designed in which the CDR hypervariable regions plus a varying number of framework residues from 132E09 were grafted onto human V-region acceptor frameworks.

Ten grafted VL regions (gL 1-10) were designed and genes were built by oligonucleotide assembly and PCR mutagenesis. A total of 13 grafted VH regions were also constructed (gH1-13) using two different framework regions, VH3 1-4 3-72 and VH3 1-3 3-21. The light chain grafted sequences were sub-cloned into the human light chain expression vector pKH10.1 which contains the DNA encoding the human C-Kappa constant region (Km3 allotype). The heavy chain grafted sequences were sub-cloned into the human gamma-4 expression vector pVhg4P FL, which contains the DNA encoding the human gamma-4 constant region containing the hinge stabilising mutation S241P (Angal et al., supra). Plasmids were cotransfected into CHO cells and the antibodies produced screened for activity in IL-6 binding and in vivo assays. Transfections of CHO cells were performed using the Lipofectamine™ 2000 procedure according to manufacturer's instructions (InVitrogen, catalogue No. 11668).

Of the 13 heavy chain grafts produced, two contained only a single framework donor residue (Ala) at position 49 and these were produced using both of the two different heavy chain frameworks. The VH3 1-3 3-21 graft expressed poorly in CHO cells and showed a reduced affinity for IL-6. In contrast, the graft using the VH3 1-4 3-72 framework expressed well and retained the affinity of the donor antibody. This heavy chain graft, comprising only a single donor framework residue, was selected in combination with the light chain graft gL10 in which only the CDRs were transferred.

FIG. 1 shows an alignment between the donor rat sequence 132E09 and the acceptor human frameworks. The heavy chain acceptor framework is the human germline sequence VH3 1-3 3-72, with framework 4 coming from this portion of the human JH-region germline JH4. The light chain acceptor framework is the human germline sequence VK1 2-1-(1) 012, with framework 4 coming from this portion of the human JK-region germline JK2. The graft sequences for gH13 and gL10 are shown in FIG. 1 (SEQ ID NOS: 11, 12, 13 and 14).

This grafted antibody was termed CA030_00240.g1. This was produced as a whole IgG4 comprising the serine to proline substitution at position 241 as describe above. The complete translated heavy and light chain sequences are shown in FIGS. 2a and 2b respectively. The complete amino acid sequence of the heavy chain is provided in SEQ ID NO: 16 and the light chain in SEQ ID NO: 18. The DNA sequence encoding the heavy and the light chain are provided in SEQ ID NOS: 15 and 17 respectively. Nucleotides 1-57 in SEQ ID NO: 15 and in FIG. 2a encode the signal peptide sequences from mouse antibody B72.3 VH and nucleotides 1-60 in SEQ ID NO: 17 and in FIG. 2b encode the signal peptide sequences from mouse antibody B72.3 VL.

Mouse antibody B72.3 is described in Whittle et al., 1987, Protein Eng. 1(6) 499-505.

EXAMPLE 3

Binding Affinity

CA030_00240.g1 Binding Affinity Measurements

The BIAcore technology monitors the binding between biomolecules in real time and without the requirement for labelling. One of the interactants, termed the ligand, is either immobilised directly or captured on the immobilised surface while the other, termed the analyte, flows in solution over the captured surface. The sensor detects the change in mass on the sensor surface as the analyte binds to the ligand to form a complex on the surface. This corresponds to the association process. The dissociation process is monitored when the analyte is replaced by buffer. In the affinity BIAcore assay, the ligand is CA030_00240.g1 whole IgG4 and the analyte is human IL-6.

Instrument
  Biacore® 3000, Biacore AB, Uppsala, Sweden
Sensor Chip
  CM5 (research grade) Catalogue Number: BR-1001-14, Biacore AB, Uppsala, Sweden. Chips were stored at 4° C.
BIAnormalising Solution
  70% (w/w) Glycerol. Part of BIAmaintenance Kit Catalogue Number: BR-1002-51, Biacore AB, Uppsala, Sweden. The BIAmaintenance kit was stored at 4° C.
Amine Coupling Kit
  Catalogue Number: BR-1000-50, Biacore AB, Uppsala, Sweden.
  Ethyl-3-(3-dimethylaminopropyl) carbodiimide hydrochloride (EDC). Made up to 75 mg/mL in distilled water and stored in 200 µL aliquots at −70° C.
  N-Hydroxysuccinimide (NHS). Made up to 11.5 mg/mL in distilled water and stored in 200 µL aliquots at −70° C.
  M Ethanolamine hydrochloride-NaOH pH 8.5. Stored in 200 µL aliquots at −70° C.
Buffers
  Running buffer: HBS-EP (being 0.01 M HEPES pH 7.4, 0.15 M NaCl, 3 mM EDTA, 0.005% Surfactant P20). Catalogue Number: BR-1001-88, Biacore AB, Uppsala, Sweden. Buffer stored at 4° C.
  Immobilisation buffer: Acetate 5.0 (being 10 mM sodium acetate pH 5.0). Catalogue number: BR-1003-51, Biacore AB, Uppsala, Sweden. Buffer stored at 4° C.
Ligand Capture
  Affinipure F(ab')$_2$ fragment goat anti-human IgG, Fc fragment specific. Jackson ImmunoResearch Inc (Pennsylvania, USA) Catalogue number: 109-006-098. Reagent stored at 4° C.
Analyte
  Recombinant human IL-6 (R&D Systems Europe Ltd, Abingdon, Oxon. Catalogue number 206-IL-050, Lot number A131402A) stored at −70° C. and thawed once for each assay.
  Recombinant cynomologous monkey IL-6 and recombinant Rhesus monkey IL6 were produced by transiently transfection of CHO cells. The material was used as non-purified and unquantified cell culture supernatant.
Regeneration Solution
  40 mM HCl prepared by dilution with distilled water from an 11.6 M stock solution (BDH, Poole, England. Catalogue number: 101254H).
  mM NaOH prepared by dilution with distilled water from a 50 mM stock solution. Catalogue number: BR-1003-58, Biacore AB, Uppsala, Sweden.
Assay Method
  BIA (Biamolecular Interaction Analysis) was performed using a BIAcore 3000 (BIAcore AB). Affinipure F(ab')$_2$ Fragment goat anti-human IgG, Fc fragment specific (Jackson ImmunoResearch) was immobilised on a CM5 Sensor Chip via amine coupling chemistry to a capture level of ≈5000 response units (RUs). HBS-EP buffer (10 mM HEPES pH 7.4, 0.15 M NaCl, 3 mM EDTA, 0.005% Surfactant P20, BIAcore AB) was used as the running buffer with a flow rate of 10 µl/min. A 10 µl injection of CA030_240.g1 at 4 µg/mL was used for capture by the immobilised anti-human IgG-Fc. Human IL-6 was titrated over the captured CA030_240.g1 at various concentrations at a flow rate of 30 µL/min. The surface was regenerated by a 10 µL injection of 40 mM HCl, followed by a 5 µL, injection of 5 mM NaOH at a flowrate of 10 µL/min.

Background subtraction binding curves were analysed using the BIAevaluation software (version 3.2) following standard procedures. Kinetic parameters were determined from the fitting algorithm.

One batch of CA030_240.g1 was used in this study. The affinity was measured at human IL-6 concentrations at or below 20 nM. The affinity value determined for CA030_240.g1 was in the range 9.02-10.50 pM with a mean±s.e.m. of 9.76±0.74 pM (Table 1.1). It was not possible to measure the affinity with the human IL-6 immobilised on the BIAcore chip as immobilising the IL-6 resulted in a loss of native conformation.

Because it was not possible to quantify the Cynomologous monkey or Rhesus monkey IL-6 it was also not possible to determine true kinetic parameters for their interaction with CA030_00240.g1. However, visual inspection of the binding sensorgrams indicates that CA030_00240.g1 binds these non-human primate IL-6's with a similar affinity to that for human IL-6.

TABLE 1.1

Affinity of CA030 240.g1 for human IL-6.

| Reference | $k_a$ (M$^{-1}$s$^{-1}$) | $k_d$ (S$^{-1}$) | $K_d$ (M) | $k_d$ pM |
|---|---|---|---|---|
| 10017474/39-51 | 7.31E+05 | 7.68E−06 | 1.05E−11 | 10.5 |
| 10017474/39-51 | 8.52E+05 | 7.68E−06 | 9.02E−12 | 9.02 |

EXAMPLE 5

In Vitro Neutralisation Assays

The potency of antibody CA030_00240.g1, henceforth abbreviated to 240.g1, was determined using two different assays. The first assay employed a mouse IL-6 dependent cell line, called T1165, that proliferates in response to mouse, rhesus, cynomolgus and human IL-6. This direct signalling of IL-6 to cell surface IL-6 receptor, in conjunction with a signalling receptor sub-unit called gp130, is termed cis-signalling. The second assay used human umbilical vein endothelial cells (HUVECs) stimulated with IL-6 plus soluble IL-6 receptor (IL-6R) with the readout being production of monocyte chemoatractant protein-1 (MCP-1). In this assay IL-6 was either added exogenously or could be produced by stimulating HUVECs with the cytokine interleukin-17 (IL-17). These two assay variants were termed trans-signalling as HUVECs do not express IL-6R and can only respond i.e. produce MCP-1 when IL-6 and soluble IL-6R are both added exogenously.

Using these various assays it was possible to generate ND50 (neutralisation dose 50%) values for 240.g1 against human (recombinant and natural), rhesus, cynomolgus and mouse IL-6.

Materials

Culture Medium

T1165 culture medium—RPMI1640, supplemented with 10% foetal calf serum, penicillin (100 units/ml), streptomycin (50 µg/ml), glutamine (2 mM) and 10 ng/ml of human recombinant IL-6, R&D systems, UK.

HUVEC culture medium—Large vessel endothelium cell basal medium (LVECBM) TCS Cellworks, UK, large vessel endothelial cell growth supplement TCS Cellworks, UK and antibiotic supplement TCS Cellworks, UK.

CA 030_00240.g1 produced in house at a concentration of 6.83 mg/ml in PBS.

Human IL-6 R&D systems, UK, Human mammalian-derived IL-6 (derived in house from CHO transfection with human IL-6 10017108/67), rhesus IL-6 (derived in house from CHO transfection with rhesus IL-6 10017108/67), cynomolgus IL-6 (derived in house from CHO transfection with cynomolgus IL-6 10017108/67), mouse IL-6 R&D systems, UK. Antihuman MCP-1 capture antibody (555055) and anti-human MCP-1 detection antibody (554664) and human recombinant MCP-1 (890225), BD Biosciences, CA. Streptavidin-HRP (AMDEX) Amersham bioscience, UK. Thrombin Merck Biosciences, Darmstadt, Germany. sIL-6R R&D systems, UK. Human IL-17 R&D systems, UK.

T1165 assay—CellTiter 96® AQueous Promega, CA.
TM Blue (Serologicals, GA).

Measurement of 240.g1 Activity Using the IL-6 Dependent Proliferation of T1165 Cells.

T1165 cells were thawed 4 days prior to use and cultured in RPMI1640 supplemented with 10% FCS, antibiotics, glutamine and 10 ng/ml of human IL-6. Cell viability was monitored using trypan blue exclusion, only cells deemed to be at least 90% viable were used. Prior to use cells were washed, twice, in RPMI1640 in the absence of human IL-6. Cells were then counted and dispensed into 96 well flat bottomed plates at a density of 5×10$^4$/cell per well. In separate plates a serial dilution of 240.g1 was incubated in the presence of either human recombinant, human mammalian-derived (also referred to as human CHO IL-6), rhesus, cynomolgus or mouse IL-6 at a fixed concentration of 1 ng/ml (0.038 nM). The pre-mixed complex of 240.g1 and IL-6 was then transferred to wells containing T1165 cells which were incubated for 48 hours at 37° C. in a humidified 5% CO$_2$ atmosphere. During the last six hours of incubation 20 ml of CellTiter 96® AQueous was added to determine the number of proliferating cells. The inhibition of IL-6-dependent proliferation of T1165 cells by 240.g1 was expressed as a percentage inhibition of wells treated with IL-6 only minus control wells that contained cells but no IL-6.

Figure 3A:
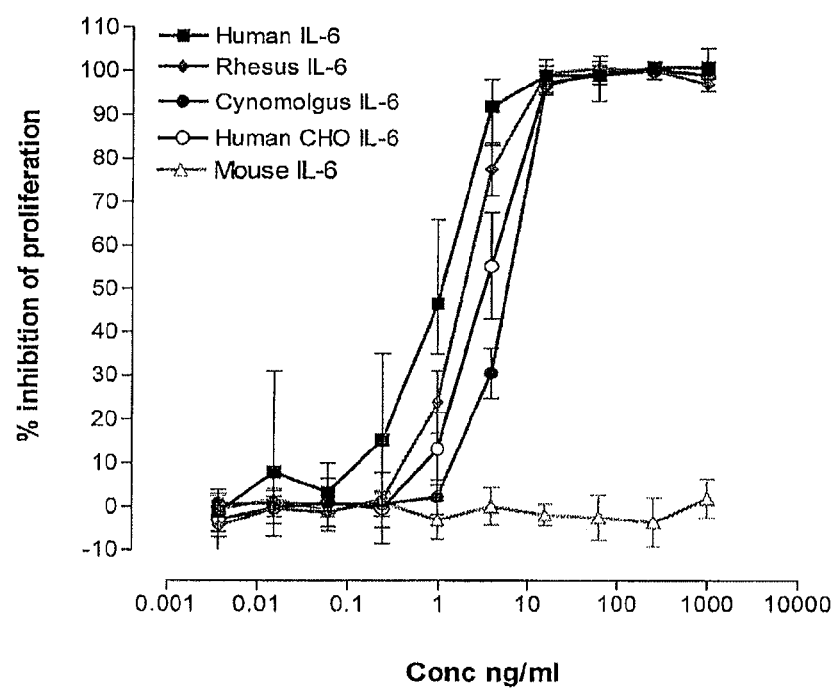
FIG. 3a shows the inhibition of human recombinant, human mammalian-derived, rhesus, cynomolgus and mouse IL-6 induced proliferation of T1165 cells by antibody 240.g1.

The activity of 240.g1 against human recombinant, human mammalian-derived, rhesus, cynomolgus and mouse IL-6 induced proliferation of the cell line T1165 can be seen in FIG. 3a. 240.g1 potently inhibited human recombinant, human mammalian-derived, rhesus, cynomolgus but not mouse IL-6 activity.

The ND50 for human recombinant IL-6 was 1.1±0.5 ng/ml (7.26±3.3 pM). The ND50 for human mammalian derived IL-6 was 3.6±2.4 ng/ml (23.76±15.84 pM). The ND50 for rhesus IL-6 was 2.2±1.1 ng/ml (14.52±7.26 pM). The ND50 for cynomolgus IL-6 was 5.4±1.1 ng/ml (35.64±7.26 pM).

Measurement of 2401.g1 Activity Using IL-6 and Soluble IL-6 Receptor Induced MCP-I Production in HUVECs.

HUVECs (TCS Cellworks, UK) were grown in large vessel endothelium cell basal medium (LVECBM) and passaged in culture no more than five times. Cells were grown until 75% confluence before use. Cells were detached using trypsin/EDTA, resuspended and washed once in fresh LVECBM. Cells were then counted and dispensed into 96 well flat bottomed plates at a density of 2×10$^4$/cells per well. Cells were then cultured overnight at 37° C. in a humidified 5% CO2 atmosphere. The next day cells were washed in fresh medium supplemented with biotinylated thrombin (3 U/ml), and set aside. In separate plates a serial dilution of 240.g1 was incubated in the presence of human recombinant IL-6 (50 ng/ml; 3.84 nM) and sIL-6R at a fixed concentration of 500 ng/ml (10.15 nM). In addition 240.g1 was also incubated with human recombinant IL-17 (25 ng/ml; 1.18 nM), which stimulates HUVECs to produce IL-6, and sIL-6R at a fixed concentration of 500 ng/ml (10.15 nM). The pre-mixed complex of 240.g1 and IL-6/sIL-6R or IL-17/sIL-6R was then transferred to wells containing HUVECs which were incubated for 24 hours at 37° C. in a humidified 5% CO$_2$ atmosphere. After the incubation period cell free supernatant was collected and human MCP-1 levels determined by sandwich ELISA (protocol given below). The inhibition of IL-6/sIL-6R or IL-17/sIL-6R induced MCP-1 production by 240.g1 was expressed as a percentage inhibition of wells treated with IL-6/sIL-6R or IL-17/sIL-6R minus control wells that contained cells but no stimuli. In addition controls were added to indicate the response of cells to the addition human IL-6 in the absence of sIL-6R.

MCP-1 ELISA

Nunc Maxisorp plates were coated with anti-MCP-1 capture antibody at a concentration of 2 pg/ml. Plates were incubated at +4° C. overnight then washed twice in PBS plus 0.1% tween20 (wash buffer). Plates were blocked for 1 hour in PBS plus 5% bovine serum albumin. Plates were then washed four times with wash buffer and standards and samples added. Plates were incubated for two hours at room temperature. Plates were then washed and biotinylated anti-MCP-1 antibody added at a concentration of 1 mg/ml. Plates were incubated for a further 2 hours then washed four times. A 1:5000 dilution of streptavidin-HRP was then added and plates incubated for 30 minutes. Plates were washed a final four times and TMB substrate was added. Colourimetric readings were taken at 630 nm and background readings at 492 nm. MCP-1 concentrations were derived, from a standard curve using a four-parameter logistic curve fit, on Genesis II software.

Figure 3B:
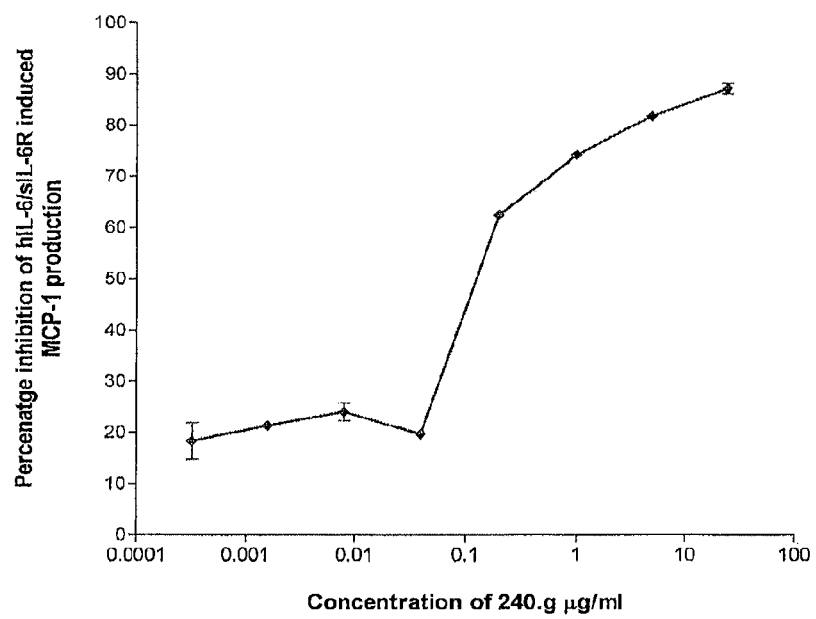
FIG. 3b shows the inhibition of human recombinant IL-6 and sIL-6R induced MCP-1 production in HUVECs by antibody 240.g1.

The activity of 240.g1 against human recombinant IL-6 and sIL-6R induced trans-signalling in HUVECs can be seen in FIG. 3b. 240.g1 potently inhibited human recombinant IL-6 and sIL-6R induced MCP-1 production by HUVECs. The ND50 was 64±62 ng/ml (422±409 pM).

Figure 3C:
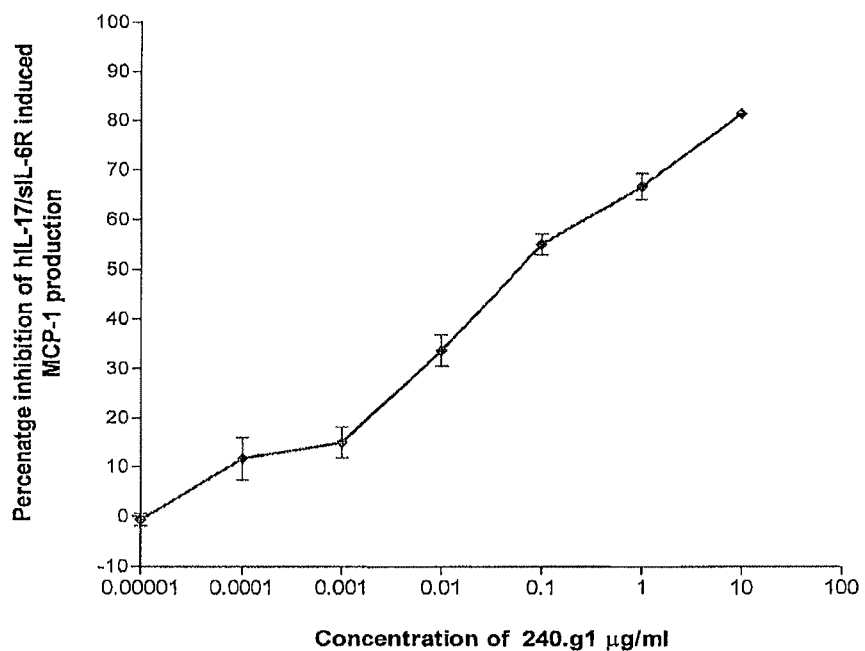
FIG. 3c shows the inhibition of IL-17 induced endogenous IL-6 and sIL-6R induced MCP-1 production in HUVECs by antibody 240.g1.

The activity of 240.g1 against IL-17 induced endogenous IL-6 and sIL-6R induced trans-signalling in HUVECs can be seen in FIG. 3c. 240.g1 potently inhibited IL-17 induced endogenous IL-6 and sIL-6R induced MCP-1 production by HUVECs. The ND50 was 93±70 ng/ml (614±462 pM).

Conclusion 240.g1 is capable of neutralising the bioactivity of human recombinant, human mammalian-derived, rhesus and cynomolgus but not mouse IL-6 in an IL-6 cis-signalling assay. In addition 240.g1 can neutralise IL-6 trans-signalling induced by either recombinant or endogenous IL-6.

EXAMPLE 6

In Vivo Activity

IL-6 is known to induce acute phase proteins. In mice the most prominent acute phase protein is serum amyloid A (SAA). Human IL-6 is able to act on the mouse receptor so it is possible to inject human IL-6 into mice and measure SAA production in the serum.

Balb/c mice were injected s.c. with the site 3 specific anti-hIL-6 antibody, CA030_240.g1 whole IgG4. 24 hours later, mice were injected i.p. with hIL-6 at 30 µg/kg (Peprotech catalogue number 200-06, lot number 0203B16). After 20 hours the blood was taken by cardiac puncture and serum collected for assessment of serum amyloid A (SAA) by ELISA (Tridelta lot number 22KT022). As noted in FIG. 4, SAA induction by hIL-6 was inhibited by CA030_240.g1 with statistically significant reduction in SAA being noted at doses of 0.3, 0.1 and 0.03 mg/kg.

n=7-8/group, except PBS n=6. Statistical analysis by ANOVA with Bonferroni post test, ** P<0.01 compared with IL-6 alone.

2 further experiments confirmed significant inhibition of IL-6 (30 g/kg)-induced SAA by CA030_240.g1 at doses of 0.3 and 0.1 mg/kg.

EXAMPLE 7

CA030 00240.21 Epitope Mapping

The epitope on human IL-6 that CA030_00240.g1 recognises was mapped using NMR technology using 240.g1 as a Fab' fragment. This required that human IL-6 was expressed in E. coli and uniformly labelled with $^{15}N/^{13}C/^{2}H$ stable isotopes. Complete sequence-specific backbone resonance assignments were obtained for free IL-6 and changes in the position of these signals induced by the binding of the Fab' fragment of CA030 00240.g1 were detected using a 3D TROSY HNCO spectrum.

Expression and Purification of Recombinant Human IL-6:

Human IL-6 was prepared from an E. coli expression vector (pET3d) containing the coding sequence of the mature form of the protein. The protein was expressed in Tuner (DE3) pLysS cells, resulting in high yields of an insoluble product. $^{15}N$, $^{15}N/^{13}C$ and $^{15}N/^{13}C/^{2}H$ labelled samples of IL-6 were prepared from cells grown on appropriately labelled rich media (Celtone).

The IL-6 was purified from transformed E. coli cells using well established procedures. Initially, cells harvested from 1 L of culture media were resuspended in 40 mL buffer A [100 mM KCl, 2 mM DTT, 10 mM Tris-HCl pH 8.5, 25% (w/v) sucrose, dissolved protease inhibitor tablet (Boehringer)]. 10 mL of buffer B [300 mM Tris-HCl pH 8.5, 100 mM EDTA, 4 mg/ml lysozyme] was added and the suspension incubated on ice for 10-30 minutes with occasional swirling. 50 ml of buffer C [1 M LiCl, 20 mM EDTA, 0.5% (v/v) NP-40] was then added and the suspension put through the French Press twice at 20,000 psi. The homogenate was then centrifuged at 16,000 g rpm for 15 minutes at 4° C. and the pellet retained. The pellet was resuspended in 40 ml buffer D [10 mM Tris-HCl pH 8.5, 0.1 mM EDTA, 0.5 M LiCl, 0.5% (v/v) NP-40, 1 mM DTT, dissolved protease tablet] and put through the French Press and centrifuged as before. This stage is repeated. The pellet is then resuspend in 40 ml buffer E [10 mM Tris-HCl pH 8.5, 0.1 mM EDTA, 0.5% (v/v) NP-40, 1 mM DTT, dissolved protease tablet] and put through French Press and centrifuged as before. Repeat this stage. The final pellet is dissolved in 6 mL 6 M GuHCl, 50 mM Tris-HCl pH 8.0 and clarified by centrifugation at 48,000 g for 30 minutes at 4° C. The supernatant is retained and the solubilised IL-6 quantified spectrophotometrically.

The solubilised IL-6 diluted to 2.5 mg/mL in 5 M GuHCl, 50 mM NaCl, 50 mM Tris-HCl, 2 mM GSH, 0.2 mM GSSG, 1 mM EDTA, pH 8.0 and incubated at 25° C. for 1 hour. The samples was then further diluted, in a drop wise fashion to 250 g/mL in 50 mM NaCl, 50 mM Tris-HCl, 2 mM GSH, 0.2 mM GSSG, 1 mM EDTA, pH 8.0 and incubated 25° C. for 3 hours. Any precipitate formed at this stage is removed by centrifugation at 30,000 g for 30 minutes at 4° C. The clarified material is dialysed against 50 mM Tris-HCl, 10% (v/v) glycerol, pH 9.0 for a minimum of 16 hours at 4° C. with two changes of buffer. After dialysis the solution is clarified by centrifugation at 30,000 g for 30 minutes at 4° C. The supernatant is retained and loaded onto an 8 mL monoQ (Amersham Biosciences) ion exchange column and eluted with a linear gradient of sodium chloride (0-1.0 M). Fractions containing the refolded IL-6 were identified by SDS-PAGE and then pooled and difiltered into 25 mM sodium phosphate, 100 mM NaCl, 0.01% (w/v) $NaN_3$, pH 6.5.

The Fab' fragment of CA030_00240.g1 was generated, purified and formulated in 25 mM sodium phosphate, 100 mM NaCl, 0.01% (w/v) $NaN_3$, pH 6.5. The 1:1 complexes between IL-6 and the Fab' fragment of CA030_00240.g1 was prepared for NMR analysis by mixing equimolar amounts of the proteins at a concentration of about 0.2-0.6 mM.

NMR Spectroscopy:

The NMR experiments were carried out on 0.35 ml samples of the proteins and complexes in a 25 mM sodium phosphate, 100 mM sodium chloride and 0.01% (w/v) sodium azide buffer at pH 6.5 (95% H$_2$O and 5% D$_2$O). The 1:1 complex between $^{15}$N/$^{13}$C/$^2$H labeled 11-6 and the unlabelled Fab' fragment of CA030_00240.g1 was prepared for NMR analysis by mixing equimolar amounts of the proteins to achieve a final concentration of 0.1 mM. The NMR data were acquired at 25° C. for free IL-6 and for the IL-6:Fab' fragment of CA030_00240.g1 complex on a 800 MHz Bruker Avance spectrometer equipped with a triple-resonance ($^{15}$N/$^{13}$C/$^2$H) cryoprobe. Standard HNCACB, CBCA (CO)NH and HNCO spectra (Wittekind, M., and Mueller, L. (1993) *J Magn Reson, Series B* 101(2), 201; Grzesiek, S., and Bax, A. (1993) *J Biomol NMR* 3(2), 185-204; Muhandiram, D. R., and Kay, L. E. (1994) *J Magn Reson, Series B* 103(3), 203; Grzesiek, S., and Bax, A. (1992) *J Magn Reson* 96(2), 432) were used to make complete sequence-specific backbone resonance assignments ($^{15}$N/$^{13}$C/$^2$H) for free 11-6 using a 0.9 mM uniformly $^{15}$N/$^{13}$C labelled sample.

Changes in the positions of IL-6 backbone signals induced by Fab' fragment of CA030 00240.g1 binding were detected using a 3D TROSY$^-$HNCO spectrum (Salzmann, M. et al., (1998) *Proc Natl Acad Sci USA* 95(23), 13585-13590). Typical acquisition parameters for all the 3D NMR experiments are provided in table 1.

All the spectra were processed using NMRPipe (Delaglio, F. et al., (1995) *J Biomol NMR* 6(3), 277-293), with linear prediction used to extend the effective acquisition time in the $^{15}$N dimension of 3D data to about 30 ms. Mild resolution enhancement was applied in all dimensions using a shifted sine-squared function. Analysis of the spectra was carried out using Sparky (Goddard, T. D., and Kneller, D. G. SPARKY 3. In., University of California, San Francisco).

Analysis of Fab Binding Data:

The minimal shift approach (Farmer, B. T. et al., (1996) *Nat Struct Mol Biol* 3(12), 995; Muskett, F. W. et al., (1998) *J Biol Chem* 273(34), 21736-21743) was used to determine the changes in the positions of IL-6 NMR signals resulting from Fab' fragment of CA030_00240.g1 binding. Initially, all peaks in the 3D HNCO spectrum of free IL-6 and 3D TROSY$^-$HNCO spectrum of IL-6 bound to g132E09 Fab were picked in their centres. The $^{15}$N and $^1$H chemical shift values of backbone resonances were corrected for the difference in temperature between spectra of the complex and free protein (−0.8 ppm for $^{15}$N and −0.05 ppm for $^1$H) (Baxter, N. J., and Williamson, M. P. (1997) *J Biomol NMR* 9(4), 359-369). The minimum change in position for peaks between free and Fab-bound IL-6 was obtained by using Microsoft Excel to calculate the combined chemical shift difference in $^{15}$N, $^{13}$C and $^2$H for each assigned peak in the HNCO spectrum of the free protein compared to all observed peaks in TROSY$^-$HNCO spectrum of Fab complex. The combined amide proton, nitrogen and carbon chemical shift differences ($\Delta\delta$) were defined according to the following equation (Equation 1), where $\Delta\delta_{HN}$, $\Delta\delta_N$ and $\Delta\delta_C$ correspond to the differences in $^1$H, $^{15}$N and $^{13}$C shifts between pairs of compared HNCO peaks and aN and ac are scaling factors of 0.2 and 0.33 required to account for differences in the range of amide proton, amide nitrogen and carbon chemical shifts. For each individual HNCO peak, the minimal shift induced by Fab binding was taken as the lowest possible combined shift value (AO).

$$\Delta\delta = \sqrt{(\Delta\delta_{HN})^2 + (\Delta\delta_N \alpha_N)^2 + (\Delta\delta_C \alpha_C)^2} \quad \text{(Eq. 1)}$$

To identify the Fab binding sites (epitopes) on IL-6, a histogram of combined minimal shift versus protein sequence was used to reveal regions of IL-6 containing significantly perturbed signals. If the size of the combined chemical shift change for individual amino acids exceeded a threshold value of the mean of the combined chemical shift change for all the amino acids plus one standard deviation from that mean, these residues were selected for further evaluation as possible contact residues in the Fab binding site. The locations of candidate binding site residues were finally examined on the high resolution structure of IL-6 (Xu, G. Y. et al., (1997) *J Mol Biol* 268(2), 468-481) and only residues positioned on the protein surface were considered to be available for Fab binding.

Two different thresholds were applied to identify residues bound by the Fab, the mean minimal shift+1 SD (0.143) and the mean minimal shift+2SD (0.213). The binding site of the antibody was found to encompass the critical site 3 signature residue of Trp157 (Boulanger et al., 2003, Science, 300, 2101-2104). Using the amino acid numbering used in Boulanger et al., supra the antibody 240g.1 was found to bind at least the following residues (mean+2SD (0.213)) S47, C50, E93, R104, F105, E106, T149, K150, A153, Q156, Q159 and S169. The antibody may bind all of the following residues (mean+1SD (0.143)) C44, S47, C50, S53, A58, E93, V96, R104, F105, E106, T149, K150, Q152, A153, Q154, N155, Q156, W157, Q159, T163, L165, S169 and E172.

It will be appreciated that the same residues may also be numbered based on the amino acid numbering of the unprocessed precursor of IL-6 (Swiss Prot Accession number P05231). Using this numbering the antibody 240g.1 binds to at least the following residues S75, C78, E121, R132, F133, E134, T177, K178, A181, Q182, Q187 and S197. The antibody may bind all of the following residues C72, S75, C78, S81, A86, E121, V124, R132, F133, E134, T177, K178, Q180, A181, Q182, N183, Q184, W185, Q187, T191, L193, S197 and E200.

TABLE 1

Basic parameters of NMR experiments.

| Experiment | Indirect dimension | Sweep width [ppm] | Carrier offset [ppm] | Acquisition time [ms] |
|---|---|---|---|---|
| HNCACB and | $^{15}$N (F2) | 35 | 117.5 | 23.4 |
| CBCA(CO)NH | $^{13}$C (F1) | 70 | 44.7 | 9.6 (6.6) |
| HNCO | $^{15}$N (F2) | 35 | 117.5 | 23 |
|  | $^{13}$C (F1) | 12 | 177.5 | 17.7 |
| TROSY-HNCO | $^{15}$N (F2) | 35 | 117.5 | 17.6 |
|  | $^{13}$C (F1) | 14 | 177.5 | 17.6 |

The direct $^1$H dimension (F3 or F2) was acquired with a sweep width of 14 ppm and acquisition time of 85 ms.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

What is claimed is:

1. A cloning or expression vector comprising DNA comprising nucleotides 58-2008 of SEQ ID NO:15 and nucleotides 61-705 of SEQ ID NO:17.

2. A cultured host cell comprising the cloning or expression vector according to claim 1.

3. A process for the production of an antibody having binding specificity for human IL-6, comprising culturing a host cell comprising a vector or vectors comprising 1) a DNA encoding the heavy chain of the antibody or variable region thereof, wherein said DNA comprises a sequence selected from the group consisting of SEQ ID NO:12, SEQ ID NO:15, or nucleotides 58-2008 of SEQ ID NO:15 and 2) a DNA encoding the light chain of the antibody or variable region thereof, wherein said DNA comprises a sequence selected from the group consisting of SEQ ID NO:14, SEQ ID NO:17, or nucleotides 61-705 of SEQ ID NO:17, under conditions suitable for the expression of the antibody and isolating the antibody.

* * * * *

SEQUENCE LISTING

<160> NUMBER OF SEQ ID NOS: 25

<210> SEQ ID NO 1
<211> LENGTH: 357
<212> TYPE: DNA
<213> ORGANISM: Rattus rattus

<400> SEQUENCE: 1

```
gaggtgcaaa ttttggagac tggaggaggc ttggtgaagc ccggtggttc cctgagactg      60
tcttgtgcaa cgtctggatt caacttcaat gattatttca tgaactgggt ccgtcaggct     120
ccagggaagg gactagagtg gcttgctcaa atgagaaaca aaattatca atatggcaca      180 tattatgcgg agtctttgga aggcagagtc acagtctcac gagacgatgc caaaaacagt     240
gtctacctgc aagtgagcag tttaagagct gaggacacgg ccatttatta ctgtacaaga     300
gagtcatact acggctttac ctcctactgg ggccaaggag tcatggtcac agtctcg       357
```

<210> SEQ ID NO 2
<211> LENGTH: 120
<212> TYPE: PRT
<213> ORGANISM: Rattus rattus

<400> SEQUENCE: 2

Glu Val Gln Ile Leu Glu Thr Gly Gly Gly Leu Val Lys Pro Gly Gly
1               5                   10                  15

Ser Leu Arg Leu Ser Cys Ala Thr Ser Gly Phe Asn Phe Asn Asp Tyr
            20                  25                  30

Phe Met Asn Trp Val Arg Gln Ala Pro Gly Lys Gly Leu Glu Trp Leu
        35                  40                  45

Ala Gln Met Arg Asn Lys Asn Tyr Gln Tyr Gly Thr Tyr Tyr Ala Glu
    50                  55                  60

Ser Leu Glu Gly Arg Val Thr Val Ser Arg Asp Asp Ala Lys Asn Ser
65                  70                  75                  80

Val Tyr Leu Gln Val Ser Ser Leu Arg Ala Glu Asp Thr Ala Ile Tyr
                85                  90                  95

Tyr Cys Thr Arg Glu Ser Tyr Tyr Gly Phe Thr Ser Tyr Trp Gly Gln
            100                 105                 110

Gly Val Met Val Thr Val Ser Ser
        115                 120

<210> SEQ ID NO 3
<211> LENGTH: 321
<212> TYPE: DNA
<213> ORGANISM: Rattus rattus

<400> SEQUENCE: 3

```
gacatccaga tgacacagtc tcctgcctcc ctgtctgcat ctctggaaga aattgtcacc      60
atcacatgcc aggcaagcca ggacattggt atttctttat catggtatca gcagaaacca     120
gggaggactc ctcagctcct gatccaaaat gcaaacaact ggcagatgg ggtcccatca     180 aggttcagcg gccgtagatt tggcacacag ttttctctta cgatcagtac accacaggtt     240
gaagatactg gagtctatta ctgtctccag cataatagtg ctccgtacac gtttggaact     300
gggacccagc tggaaatcaa a                                               321
```

<210> SEQ ID NO 4
<211> LENGTH: 108
<212> TYPE: PRT
<213> ORGANISM: Rattus rattus

<400> SEQUENCE: 4

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Ile Ser
            20                  25                  30

Leu Ser Trp Tyr Gln Gln Lys Pro Gly Arg Thr Pro Gln Leu Leu Ile
        35                  40                  45

Gln Asn Ala Asn Asn Leu Ala Asp Gly Val Pro Ser Arg Phe Ser Gly
    50                  55                  60

Arg Arg Phe Gly Thr Gln Phe Ser Leu Thr Ile Ser Thr Pro Gln Val
65                  70                  75                  80

Glu Asp Thr Gly Val Tyr Tyr Cys Leu Gln His Asn Ser Ala Pro Tyr
                85                  90                  95

Thr Phe Gly Thr Gly Thr Gln Leu Glu Ile Lys Arg
            100                 105

<210> SEQ ID NO 5
<211> LENGTH: 10
<212> TYPE: PRT
<213> ORGANISM: Rattus rattus

<400> SEQUENCE: 5

Gly Phe Asn Phe Asn Asp Tyr Phe Met Asn
1               5                   10

<210> SEQ ID NO 6
<211> LENGTH: 19
<212> TYPE: PRT
<213> ORGANISM: Rattus rattus

<400> SEQUENCE: 6

Gln Met Arg Asn Lys Asn Tyr Gln Tyr Gly Thr Tyr Tyr Ala Glu Ser
1               5                   10                  15

Leu Glu Gly

<210> SEQ ID NO 7
<211> LENGTH: 9
<212> TYPE: PRT
<213> ORGANISM: Rattus rattus

<400> SEQUENCE: 7

Glu Ser Tyr Tyr Gly Phe Thr Ser Tyr
1               5

<210> SEQ ID NO 8
<211> LENGTH: 11
<212> TYPE: PRT
<213> ORGANISM: Rattus rattus

<400> SEQUENCE: 8

Gln Ala Ser Gln Asp Ile Gly Ile Ser Leu Ser
1               5                   10

<210> SEQ ID NO 9
<211> LENGTH: 7
<212> TYPE: PRT
<213> ORGANISM: Rattus rattus

<400> SEQUENCE: 9

Asn Ala Asn Asn Leu Ala Asp

<210> SEQ ID NO 10
<211> LENGTH: 9
<212> TYPE: PRT
<213> ORGANISM: Rattus rattus

<400> SEQUENCE: 10

Leu Gln His Asn Ser Ala Pro Tyr Thr
1               5

<210> SEQ ID NO 11
<211> LENGTH: 120
<212> TYPE: PRT
<213> ORGANISM: Artificial
<220> FEATURE:
<223> OTHER INFORMATION: grafted heavy chain variable region gH13

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Gly Lys Gly Leu Glu Trp Val
        35                  40                  45

Ala Gln Met Arg Asn Lys Asn Tyr Gln Tyr Gly Thr Tyr Tyr Ala Glu
    50                  55                  60

Ser Leu Glu Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Ser Tyr Tyr Gly Phe Thr Ser Tyr Trp Gly Gln
            100                 105                 110

Gly Thr Leu Val Thr Val Ser Ser
        115                 120

<210> SEQ ID NO 12
<211> LENGTH: 360
<212> TYPE: DNA
<213> ORGANISM: Artificial
<220> FEATURE:
<223> OTHER INFORMATION: grafted heavy chain variable region gH13

<400> SEQUENCE: 12
gaagtccagc tcgttgagag tggcggtggc ctggtccagc ccggtggatc actccgactg      60
tcctgcgctg caagcgggtt taatttaat gattacttca tgaactgggt tcggcaggca     120
cctggcaaag gcctggaatg ggtggctcag atgaggaaca agaattatca gtacgggaca     180
tactatgccg agagtctgga gggaaggttc accatctcca gggacgattc taagaacagc     240
ctctaccttc agatgaactc tttgaaaacc gaggacacag ccgtgtacta ttgtgctaga     300
gaaagttatt acgggttcac atcttattgg ggacagggaa ccctggtgac tgtctcgagc     360

<210> SEQ ID NO 13
<211> LENGTH: 108
<212> TYPE: PRT
<213> ORGANISM: Artificial
<220> FEATURE:
<223> OTHER INFORMATION: grafted light chan variable region gL10

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Ile Ser
            20                  25                  30

Leu Ser Trp Tyr Gln Gln Lys Pro Gly Lys Ala Pro Lys Leu Leu Ile
            35                  40                  45

Tyr Asn Ala Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Leu Gln His Asn Ser Ala Pro Tyr
                85                  90                  95

Thr Phe Gly Gln Gly Thr Lys Leu Glu Ile Lys Arg
            100                 105
```

<210> SEQ ID NO 14
<211> LENGTH: 324
<212> TYPE: DNA
<213> ORGANISM: Artificial
<220> FEATURE:
<223> OTHER INFORMATION: grafted light chan variable region gL10

<400> SEQUENCE: 14

```
gatatccaga tgactcaatc acccagttcc ctgagcgcct ctgtcggcga cagggtgacc      60
atcacatgcc aggcctctca agacattggc atcagcctgt cctggtacca gcaaaaaccc    120
ggcaaggccc ctaagctcct gatctacaat gctaacaacc tggccgatgg cgtgcctagt    180
aggtttagcg gtctggttc cggaacagat ttcacactca ccatcagctc actgcagccc    240
gaggacttcg ccacttacta ttgcctgcag cacaacagcg cccccctaca cttcggacaa    300
ggcactaaac tggagatcaa gcgt                                           324
```

<210> SEQ ID NO 15
<211> LENGTH: 2008
<212> TYPE: DNA
<213> ORGANISM: Artificial
<220> FEATURE:
<223> OTHER INFORMATION: 240g1 heavy chain

<400> SEQUENCE: 15

```
atggagtgga gctgggtgtt tttgttcttc ctgtccgtga ccacaggcgt gcactctgaa      60
gtccagctcg ttgagagtgg cggtggcctg gtccagcccg gtggatcact ccgactgtcc    120
tgcgctgcaa gcgggtttaa ttttaatgat tacttcatga ctgggttcg gcaggcacct    180
ggcaaaggcc tggaatgggt ggctcagatg aggaacaaga attatcagta cgggacatac    240
tatgccgaga gtctggaggg aaggttcacc atctccaggg acgattctaa gaacagcctc    300
taccttcaga tgaactcttt gaaaaccgag gacacagccg tgtactattg ctagagaa    360
agttattacg ggttcacatc ttattgggga caggaacccc tggtgactgt ctcgagcgct    420
tctacaaagg gcccatccgt cttccccctg gcgccctgct ccaggagcac ctccgagagc    480
acagccgccc tgggctgcct ggtcaaggac tacttcccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac gaagacctac    660
acctgcaacg tagatcacaa gcccagcaac accaaggtgg acaagagagt tggtgagagg    720
ccagcacagg gagggagggt gtctgctgga agccaggctc agccctcctg cctggacgca    780
```

```
cccccggctgt gcagcccag cccagggcag caaggcatgc cccatctgtc tcctcacccg    840
gaggcctctg accaccccac tcatgccag ggagagggtc ttctggattt ttccaccagg    900
ctccgggcag ccacaggctg gatgcccta ccccaggccc tgcgcataca ggggcaggtg    960
ctgcgctcag acctgccaag agccatatcc gggaggaccc tgcccctgac ctaagcccac   1020
cccaaaggcc aaactctcca ctccctcagc tcagacacct tctctcctcc cagatctgag   1080
taactcccaa tcttctctct gcagagtcca aatatggtcc cccatgccca ccatgcccag   1140
gtaagccaac ccaggcctcg ccctccagct caaggcggga caggtgccct agagtagcct   1200
gcatccaggg acaggcccca gccgggtgct gacgcatcca cctccatctc ttcctcagca   1260
cctgagttcc tggggggacc atcagtcttc ctgttccccc aaaacccaa ggacactctc    1320 atgatctccc ggaccctga ggtcacgtgc gtggtggtgg acgtgagcca ggaagacccc    1380
gaggtccagt tcaactggta cgtggatggc gtggaggtgc ataatgccaa gacaaagccg   1440
cgggaggagc agttcaacag cacgtaccgt gtggtcagcg tcctcaccgt cctgcaccag   1500
gactggctga acggcaagga gtacaagtgc aaggtctcca caaaggcct ccgtcctcc    1560 atcgagaaaa ccatctccaa agccaaaggt gggacccacg gggtgcgagg gccacatgga   1620
cagaggtcag ctcggcccac cctctgccct gggagtgacc gctgtgccaa cctctgtccc   1680
tacagggcag ccccgagagc acaggtgta caccctgccc ccatcccagg aggagatgac    1740
caagaaccag gtcagcctga cctgcctggt caaaggcttc tacccagcg acatcgccgt    1800 ggagtgggag agcaatgggc agccggagaa caactacaag accacgcctc ccgtgctgga   1860
ctccgacggc tccttcttcc tctacagcag gctaaccgtg gacaagagca ggtggcagga   1920
ggggaatgtc ttctcatgct ccgtgatgca tgaggctctg cacaaccact acacacagaa   1980
gagcctctcc ctgtctctgg gtaaatga                                     2008
```

<210> SEQ ID NO 16
<211> LENGTH: 447
<212> TYPE: PRT
<213> ORGANISM: Artificial
<220> FEATURE:
<223> OTHER INFORMATION: 240g1 heavy chain

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Gly Lys Gly Leu Glu Trp Val
        35                  40                  45

Ala Gln Met Arg Asn Lys Asn Tyr Gln Tyr Gly Thr Tyr Tyr Ala Glu
    50                  55                  60

Ser Leu Glu Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Ser Tyr Tyr Gly Phe Thr Ser Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 17
<211> LENGTH: 705
<212> TYPE: DNA
<213> ORGANISM: Artificial
<220> FEATURE:
<223> OTHER INFORMATION: 240g1 light chain

<400> SEQUENCE: 17
atgagcgtgc ctacccaggt cctcggcctg ttgctgctct ggctgaccga tgcccgctgc      60
gatatccaga tgactcaatc acccagttcc ctgagcgcct ctgtcggcga cagggtgacc     120
atcacatgcc aggcctctca agacattggc atcagcctgt cctggtacca gcaaaaaccc     180
ggcaaggccc ctaagctcct gatctacaat gctaacaacc tggccgatgg cgtgcctagt     240
aggtttagcg gctctggttc cggaacagat ttcacactca ccatcagctc actgcagccc     300
gaggacttcg ccacttacta ttgcctgcag cacaacagcg cccctacac cttcggacaa      360
```

```
ggcactaaac tggagatcaa gcgtacggta gcggccccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                   705
```

<210> SEQ ID NO 18
<211> LENGTH: 214
<212> TYPE: PRT
<213> ORGANISM: Artificial
<220> FEATURE:
<223> OTHER INFORMATION: 240g1 light chain

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Ile Ser
            20                  25                  30

Leu Ser Trp Tyr Gln Gln Lys Pro Gly Lys Ala Pro Lys Leu Leu Ile
        35                  40                  45

Tyr Asn Ala Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Ala Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 19
<211> LENGTH: 100
<212> TYPE: PRT
<213> ORGANISM: Homo sapiens

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
```

```
                35                  40                  45
Gly Arg Thr Arg Asn Lys Ala Asn Ser Tyr Thr Thr Glu Tyr Ala Ala
    50                  55                  60
Ser Val Lys Gly Arg Phe Thr Ile Ser Arg Asp Asp Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg
            100

<210> SEQ ID NO 20
<211> LENGTH: 15
<212> TYPE: PRT
<213> ORGANISM: Homo sapiens

<400> SEQUENCE: 20

Tyr Phe Asp Tyr Trp Gly Gln Gly Thr Leu Val Thr Val Ser Ser
1               5                   10                  15

<210> SEQ ID NO 21
<211> LENGTH: 88
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 22
<211> LENGTH: 13
<212> TYPE: PRT
<213> ORGANISM: Homo sapiens

<400> SEQUENCE: 22

Tyr Thr Phe Gly Gln Gly Thr Lys Leu Glu Ile Lys Arg
1               5                   10

<210> SEQ ID NO 23
<211> LENGTH: 108
<212> TYPE: PRT
<213> ORGANISM: homo sapiens

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45
```

```
Tyr Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                     85                  90                  95

Thr Phe Gly Gln Gly Thr Lys Leu Glu Ile Lys Arg
                100                 105

<210> SEQ ID NO 24
<211> LENGTH: 466
<212> TYPE: PRT
<213> ORGANISM: Artificial
<220> FEATURE:
<223> OTHER INFORMATION: Full length Heavy chain including leader
      sequence

<400> SEQUENCE: 24

Met Glu Trp Ser Trp Val Phe Leu Phe Phe Leu Ser Val Thr Thr Gly
 1               5                  10                  15

Val His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Phe
             35                  40                  45

Asn Asp Tyr Phe Met Asn Trp Val Arg Gln Ala Pro Gly Lys Gly Leu
 50                  55                  60

Glu Trp Val Ala Gln Met Arg Asn Lys Asn Tyr Gln Tyr Gly Thr Tyr
 65                  70                  75                  80

Tyr Ala Glu Ser Leu Glu Gly Arg Phe Thr Ile Ser Arg Asp Asp Ser
                     85                  90                  95

Lys Asn Ser Leu Tyr Leu Gln Met Asn Ser Leu Lys Thr Glu Asp Thr
                100                 105                 110

Ala Val Tyr Tyr Cys Ala Arg Glu Ser Tyr Tyr Gly Phe Thr Ser Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300
```

```
Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 25
<211> LENGTH: 234
<212> TYPE: PRT
<213> ORGANISM: Artificial
<220> FEATURE:
<223> OTHER INFORMATION: Full length light chain including leader
      sequence

<400> SEQUENCE: 25

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Gly Ile Ser Leu Ser Trp Tyr Gln Gln Lys Pro Gly Lys Ala Pro
    50                  55                  60

Lys Leu Leu Ile Tyr Asn Ala Asn Asn Leu Ala Asp Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln His Asn
            100                 105                 110

Ser Ala Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
```

```
                    180                 185                 190
Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```